United States Patent
Mozloom, Jr. et al.

(10) Patent No.: US 12,402,912 B2
(45) Date of Patent: Sep. 2, 2025

(54) MULTI-DIAMETER CANNULA DEPTH LIMITER

(71) Applicant: Cilag GmbH International, Zug (CH)

(72) Inventors: Joseph T. Mozloom, Jr., Cincinnati, OH (US); Jeffery Bruns, Cincinnati, OH (US); Ryan McGhee, Cincinnati, OH (US); Cameron D. McLain, Deer Park, OH (US); Lauren M. Valente, Macomb, MA (US); Matthew S. Corbin, Placentia, CA (US)

(73) Assignee: Cilag GmbH International, Zug (CH)

( * ) Notice: Subject to any disclaimer, the term of this patent is extended or adjusted under 35 U.S.C. 154(b) by 170 days.

(21) Appl. No.: 17/213,304

(22) Filed: Mar. 26, 2021

(65) Prior Publication Data

US 2021/0338281 A1 Nov. 4, 2021

Related U.S. Application Data

(60) Provisional application No. 63/018,601, filed on May 1, 2020.

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 90/03* (2016.02); *A61B 2090/036* (2016.02)

(58) Field of Classification Search
CPC ......... Y10T 24/44769; Y10T 24/44983; Y10T 24/44923; Y10T 24/344; Y10T 24/44017;
(Continued)

(56) References Cited

U.S. PATENT DOCUMENTS 3,817,251 A 6/1974 Hasson
3,896,527 A * 7/1975 Miller .................. A61M 25/02
24/DIG. 22
(Continued)

FOREIGN PATENT DOCUMENTS

AU 702882 B2 3/1993
CN 106344126 B 2/2019
(Continued)

OTHER PUBLICATIONS

International Search Report and Written Opinion dated Jul. 22, 2021, for International Application No. PCT/EP2021/061421, 15 pages.
(Continued)

*Primary Examiner* — Tan-Uyen T Ho
*Assistant Examiner* — Bridget E. Rabaglia
(74) *Attorney, Agent, or Firm* — Frost Brown Todd LLP

(57) ABSTRACT

A depth limiter that is configured to couple with first and second trocar cannulas having different diameters. The depth limiter includes first and second body portions. First and second body portions each include first and second gripping surfaces. The first and second body portions are pivotably coupled together and are movable between an open configuration and a closed configuration. In the open configuration, the first and second body portions are configured to allow for axial movement of the depth limiter relative to the first and second trocar cannulas. The first gripping surfaces of the first and second body portions are configured to restrict axial movement of the depth limiter relative to the first trocar cannula in the closed configuration. The second gripping surfaces of the first and second body portions are configured to restrict axial movement of the depth limiter relative to the second trocar cannula in the closed configuration.

17 Claims, 22 Drawing Sheets

(58) Field of Classification Search
CPC ............. Y10T 24/205; Y10T 24/44778; Y10T 24/44906; Y10T 24/44932; Y10T 24/44915; Y10T 24/3444; Y10T 24/202; Y10T 24/3443; Y10T 24/3453; Y10T 24/44009; F16B 2/10; A47G 1/0611; A47G 25/485; D06F 55/02; H02G 3/32; F16L 3/237; F16L 3/22; F16L 2201/10; F16L 3/08; F16L 3/12; F16L 3/00; F16L 3/23; E04C 5/167; A61B 1/00128; A61B 1/0014; A61B 17/1227; A61B 1/018; A61B 17/083; A61B 50/20; A61B 2017/2808; A61B 46/23; A61B 17/122; B42B 5/06; G09F 3/16; Y10S 223/02; A61G 13/101; B65D 33/1675
USPC ......... 606/108; 24/545, 563, 67.3, 339, 564, 24/546, 456, 561, 338, 570, 129 R, 530; 248/74.2, 316.7, 230.7, 68.1, 316.5
See application file for complete search history.

(56) References Cited

U.S. PATENT DOCUMENTS

| | | | |
|---|---|---|---|
| 4,699,616 | A | 10/1987 | Nowak et al. |
| 5,002,557 | A | 3/1991 | Hasson |
| 5,147,316 | A | 9/1992 | Castillenti |
| 5,215,531 | A | 6/1993 | Maxson et al. |
| D338,270 | S | 8/1993 | Stephens et al. |
| 5,256,147 | A | 10/1993 | Vidal et al. |
| 5,257,975 | A | 11/1993 | Foshee |
| 5,263,939 | A | 11/1993 | Wortrich |
| 5,267,970 | A | 12/1993 | Chin et al. |
| 5,290,249 | A | 3/1994 | Foster et al. |
| 5,364,372 | A | 11/1994 | Danks et al. |
| D354,562 | S | 1/1995 | Medema |
| 5,540,675 | A | 7/1996 | Hasson |
| 5,697,913 | A | 12/1997 | Sierocuk et al. |
| 5,792,135 | A | 8/1998 | Madhani et al. |
| 5,800,451 | A | 9/1998 | Buess et al. |
| 5,817,061 | A | 10/1998 | Goodwin et al. |
| 5,833,666 | A | 11/1998 | Davis et al. |
| 5,836,913 | A | 11/1998 | Orth et al. |
| 5,855,566 | A | 1/1999 | Dunlap et al. |
| 5,951,588 | A | 9/1999 | Moenning |
| 5,957,888 | A | 9/1999 | Hinchcliffe |
| 6,432,085 | B1 | 8/2002 | Stellon et al. |
| 6,451,041 | B1 | 9/2002 | Moenning et al. |
| 6,620,173 | B2 | 9/2003 | Gerbi et al. |
| 6,632,197 | B2 | 10/2003 | Lyon |
| 6,638,265 | B1 | 10/2003 | Ternamian |
| 6,652,490 | B2 | 11/2003 | Howell |
| 6,808,492 | B2 | 10/2004 | Snyder |
| 7,235,064 | B2 | 6/2007 | Hopper et al. |
| 7,473,220 | B2 | 1/2009 | Francese et al. |
| 7,981,092 | B2 | 7/2011 | Duke |
| 8,147,453 | B2 | 4/2012 | Albrecht et al. |
| 8,226,553 | B2 | 7/2012 | Shelton, IV et al. |
| 8,251,900 | B2 | 8/2012 | Ortiz et al. |
| 8,287,503 | B2 | 10/2012 | Albrecht et al. |
| 8,479,969 | B2 | 7/2013 | Shelton, IV |
| 8,568,362 | B2 | 10/2013 | Moreno, Jr. et al. |
| 8,573,465 | B2 | 11/2013 | Shelton, IV |
| 8,579,807 | B2 | 11/2013 | Moreno, Jr. et al. |
| 8,636,686 | B2 | 1/2014 | Minnelli et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,821,527 | B2 | 9/2014 | Farnan et al. |
| 8,939,946 | B2 | 1/2015 | Albrecht et al. |
| 9,004,545 | B2 | 4/2015 | Whitaker et al. |
| 9,259,238 | B2 | 2/2016 | Albrecht et al. |
| 9,289,200 | B2 | 3/2016 | Dang et al. |
| 9,522,265 | B2 | 12/2016 | Pravong et al. |
| 9,675,379 | B2 | 6/2017 | Kucklick |
| 10,327,805 | B2 | 6/2019 | Hibner et al. |
| 10,327,809 | B2* | 6/2019 | Buyda ................ A61B 17/3421 |
| 10,576,259 | B2 | 3/2020 | Stafford |
| 10,792,069 | B2 | 10/2020 | Hall et al. |
| 10,820,924 | B2 | 11/2020 | Hall et al. |
| 11,359,751 | B2 | 6/2022 | White et al. |
| 11,712,267 | B2 | 8/2023 | McLain |
| 2005/0113856 | A1 | 5/2005 | Epstein et al. |
| 2005/0165432 | A1 | 7/2005 | Heinrich |
| 2007/0225643 | A1 | 9/2007 | Hopper et al. |
| 2009/0182282 | A1 | 7/2009 | Okihisa et al. |
| 2010/0010449 | A1 | 1/2010 | Leibowitz et al. |
| 2010/0057010 | A1 | 3/2010 | Göransson |
| 2011/0207362 | A1* | 8/2011 | Lifson ................ H01R 13/6392 |
| | | | 439/369 |
| 2013/0060084 | A1 | 3/2013 | Fouts et al. |
| 2014/0066953 | A1 | 3/2014 | Keating et al. |
| 2016/0015423 | A1 | 1/2016 | Ravikumar et al. |
| 2017/0245889 | A1 | 8/2017 | Herrell et al. |
| 2017/0311932 | A1 | 11/2017 | Rebellino |
| 2018/0199959 | A1 | 7/2018 | Lee |
| 2018/0206883 | A1 | 7/2018 | McIntyre et al. |
| 2018/0214140 | A1 | 8/2018 | Nock et al. |
| 2019/0000496 | A1 | 1/2019 | Shelton, IV et al. |
| 2019/0083071 | A1 | 3/2019 | Rebellino et al. |
| 2019/0150900 | A1 | 5/2019 | Choung et al. |
| 2019/0254703 | A1 | 8/2019 | Ciampini et al. |
| 2019/0254704 | A1 | 8/2019 | Buyda et al. |
| 2019/0380742 | A1 | 12/2019 | Hall et al. |
| 2020/0205855 | A1 | 7/2020 | Aravalli |
| 2021/0338269 | A1 | 11/2021 | Scott et al. |
| 2021/0338272 | A1 | 11/2021 | Muthuchidambaram et al. |
| 2021/0338273 | A1 | 11/2021 | Blair |
| 2021/0338274 | A1 | 11/2021 | Scott et al. |
| 2021/0338275 | A1 | 11/2021 | Vijayachandran |
| 2021/0338276 | A1 | 11/2021 | Scott |
| 2021/0338278 | A1 | 11/2021 | Scott et al. |
| 2021/0338282 | A1 | 11/2021 | Vijayachandran |
| 2021/0338283 | A1 | 11/2021 | McLain |
| 2021/0338371 | A1 | 11/2021 | Harris et al. |

FOREIGN PATENT DOCUMENTS

| | | |
|---|---|---|
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.
International Search Report and Written Opinion dated Jul. 16, 2021, for International Application No. PCT/EP2021/061442, 13 pages.
International Search Report and Written Opinion dated Jul. 8, 2021, for International Application No. PCT/EP2021/061447, 15 pages.
International Search Report and Written Opinion dated Jul. 27, 2021, for International Application No. PCT/EP2021/061456, 14 pages.
International Search Report and Written Opinion dated Jul. 13, 2021, for International Application No. PCT/EP2021/061459, 16 pages.
International Search Report and Written Opinion dated Jul. 20, 2021, for International Application No. PCT/EP2021/061466, 17 pages.
International Search Report and Written Opinion dated Jul. 15, 2021, for International Application No. PCT/EP2021/061468, 16 pages.
European Examination Report dated Jul. 26, 2023 for Application No. EP 21722871, 4 pgs.

(56) References Cited

OTHER PUBLICATIONS

European Examination Report dated Jul. 20, 2023 for Application No. EP 21723218, 5 pgs.
European Examination Report dated Sep. 15, 2023 for Application No. EP 21722865, 5 pgs.
European Examination Report dated Aug. 10, 2023 for Application No. EP 21722862, 5 pgs.

* cited by examiner

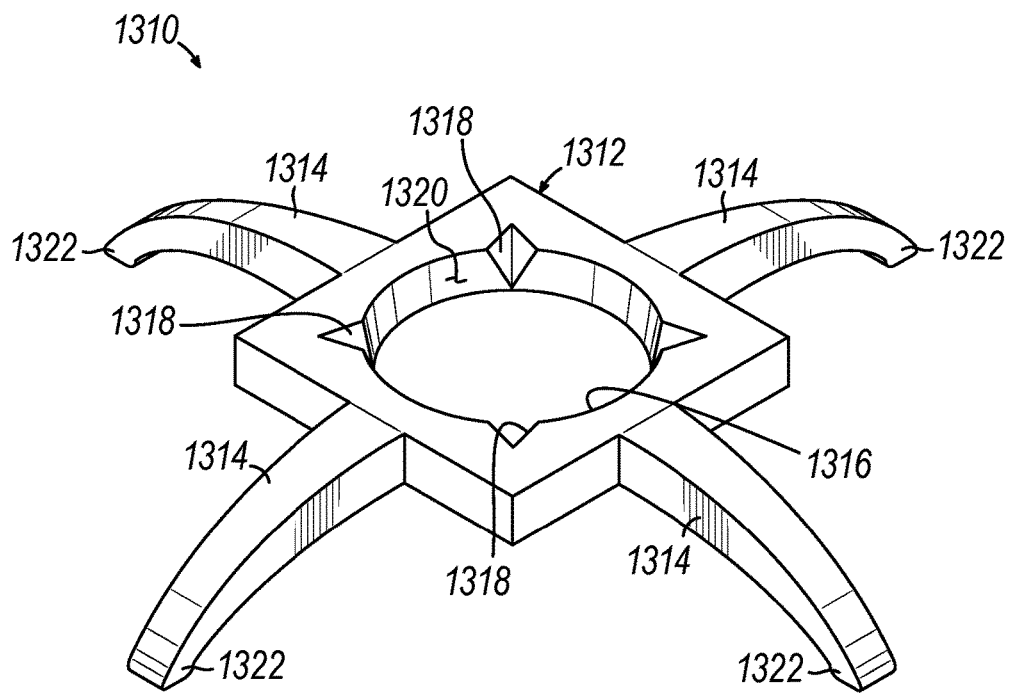
FIG. 17
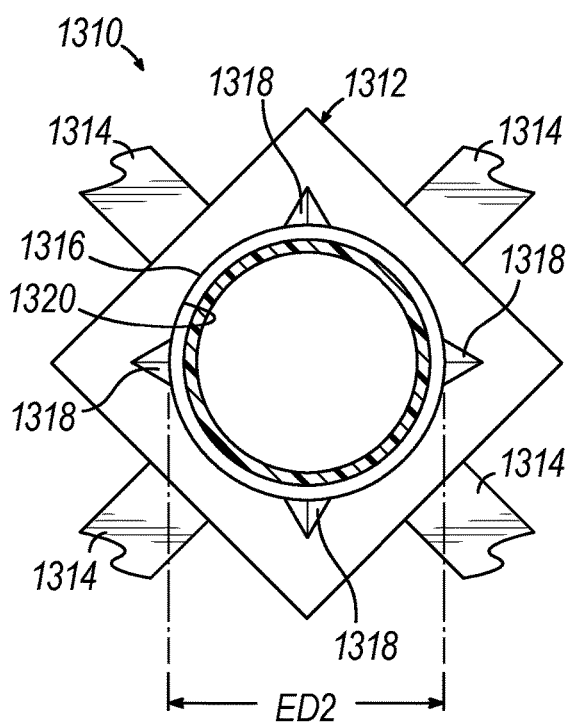 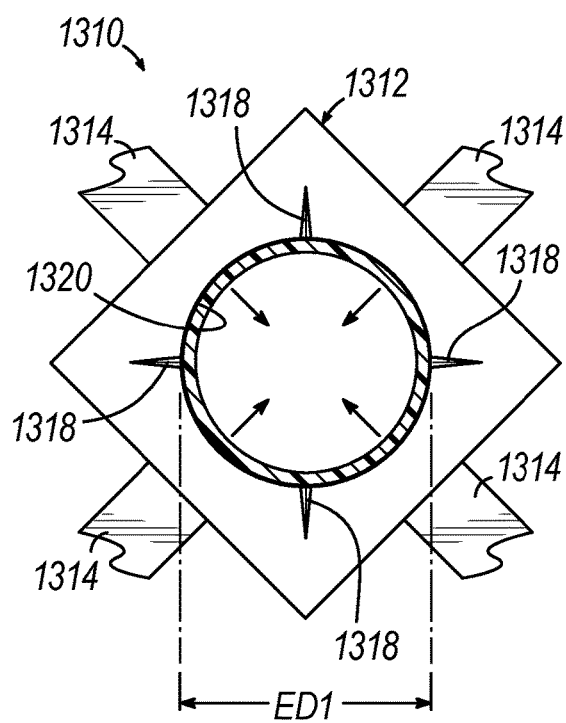
FIG. 18A  FIG. 18B

MULTI-DIAMETER CANNULA DEPTH LIMITER

PRIORITY

This application claims priority to U.S. Provisional Pat. App. No. 63/018,601, entitled "Multi-Diameter Cannula Depth Limiter," filed on May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 17 depicts a perspective view of a seventh exemplary depth limiter that includes a hub with notches;

FIG. 18A depicts a top plan view of the depth limiter of FIG. 17 coupled with the cannula tube of the cannula assembly of FIG. 5, where the hub of the depth limiter is in a movable configuration;

FIG. 18B depicts a partial side sectional view of the depth limiter of FIG. 17 coupled with the cannula tube of the cannula assembly of FIG. 5 following detachment and removal of the obturator, where the legs of the depth limiter are in a fixed configuration;

Figure 1:
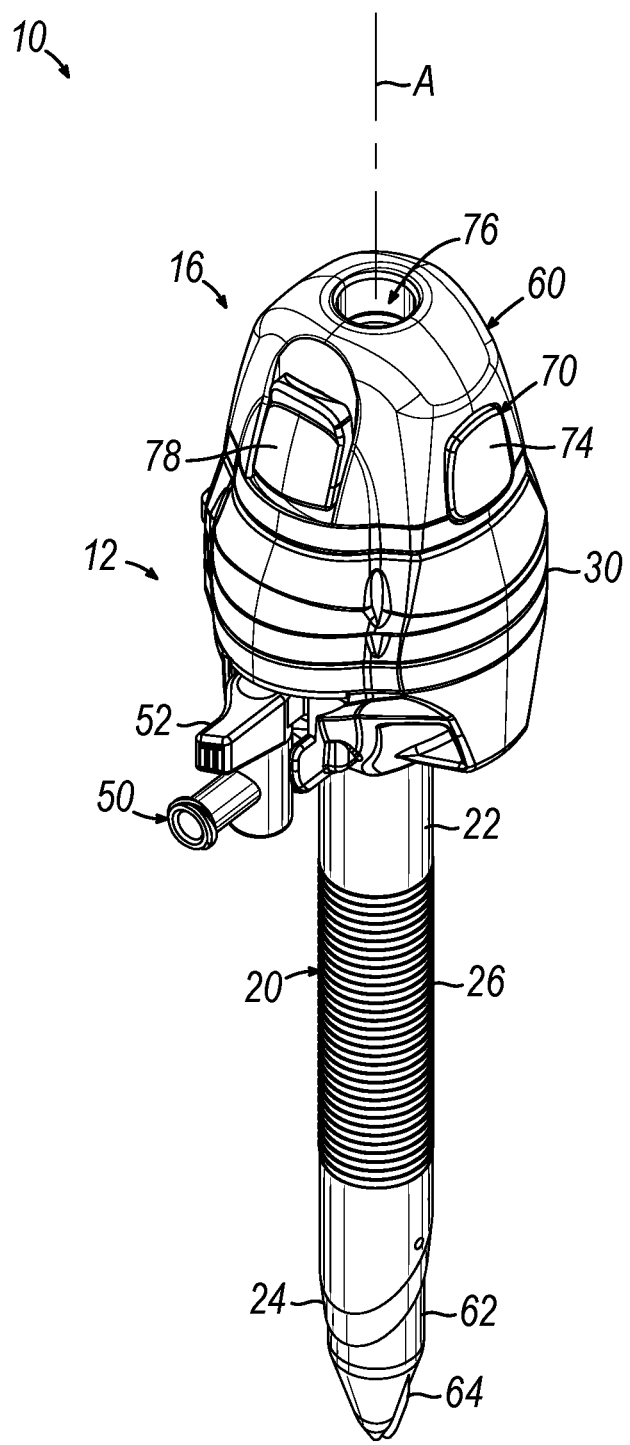
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. EXEMPLARY SINGLE-USE AND REUSABLE TROCARS

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
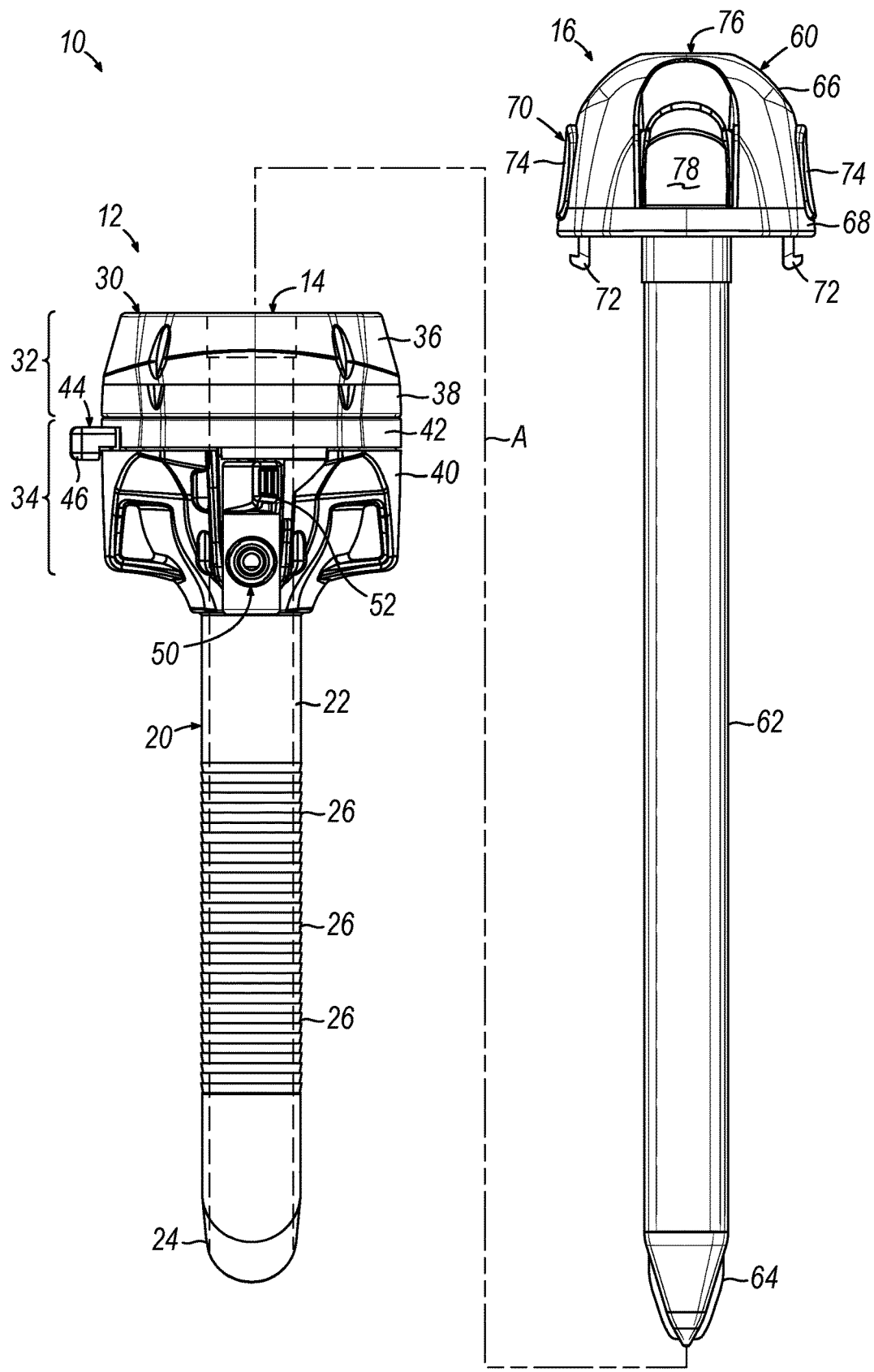
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
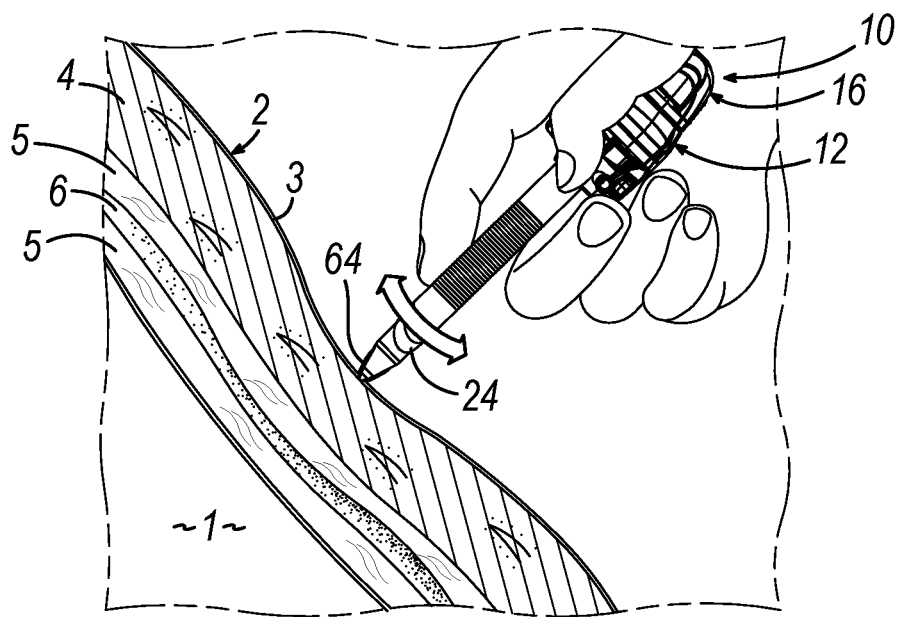
FIG. 3A depicts a side sectional view of the trocar of FIG. 1 being manipulated by a clinician through tissue layers of an abdominal wall.
Figure 3B:
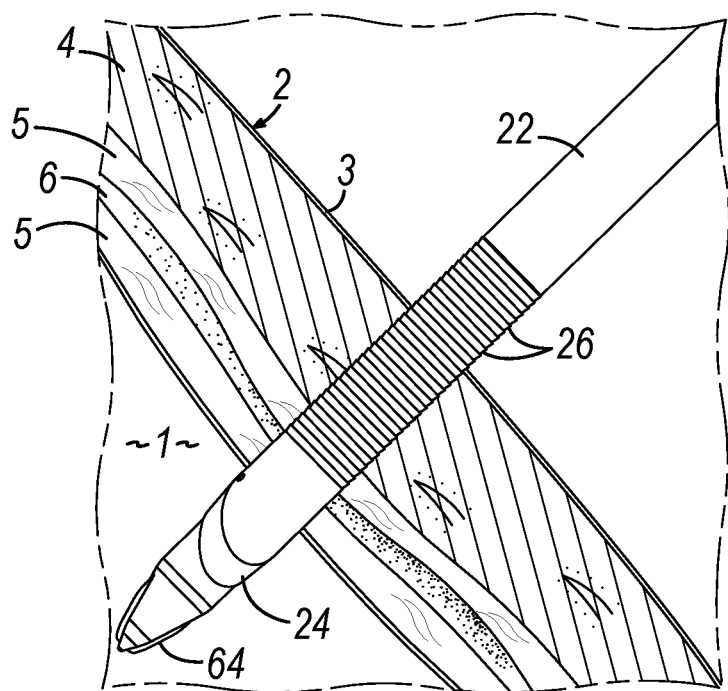
FIG. 3B depicts an enlarged side sectional view of the trocar of FIG. 1, showing a distal end of the trocar received within the abdominal cavity of FIG. 3A.
Figure 3C:
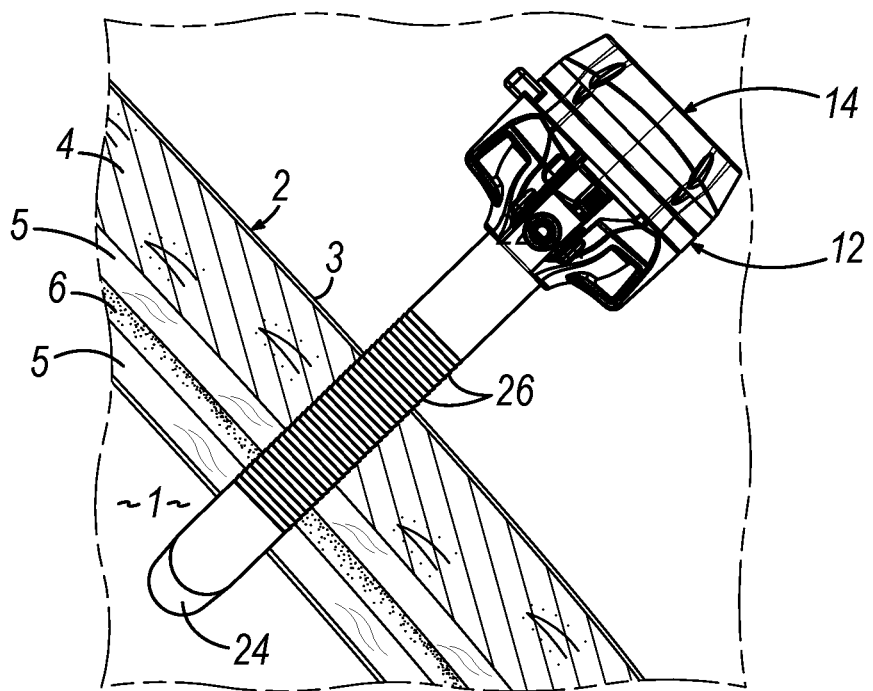
FIG. 3C depicts a side sectional view of the cannula assembly of FIG. 1, showing the cannula assembly remaining positioned within the abdominal wall of FIG. 3A following detachment and removal of the obturator.
Figure 3D:
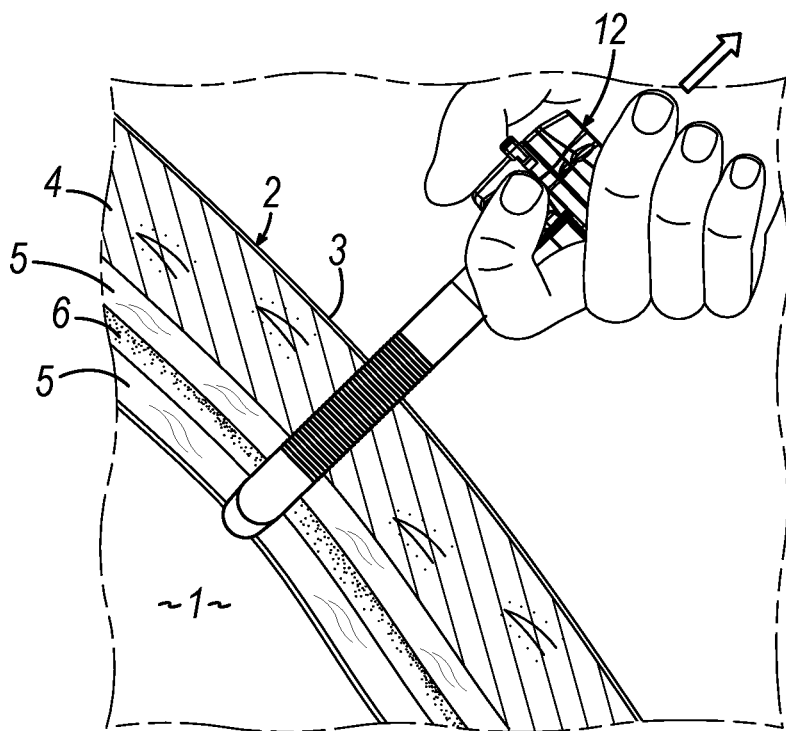
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
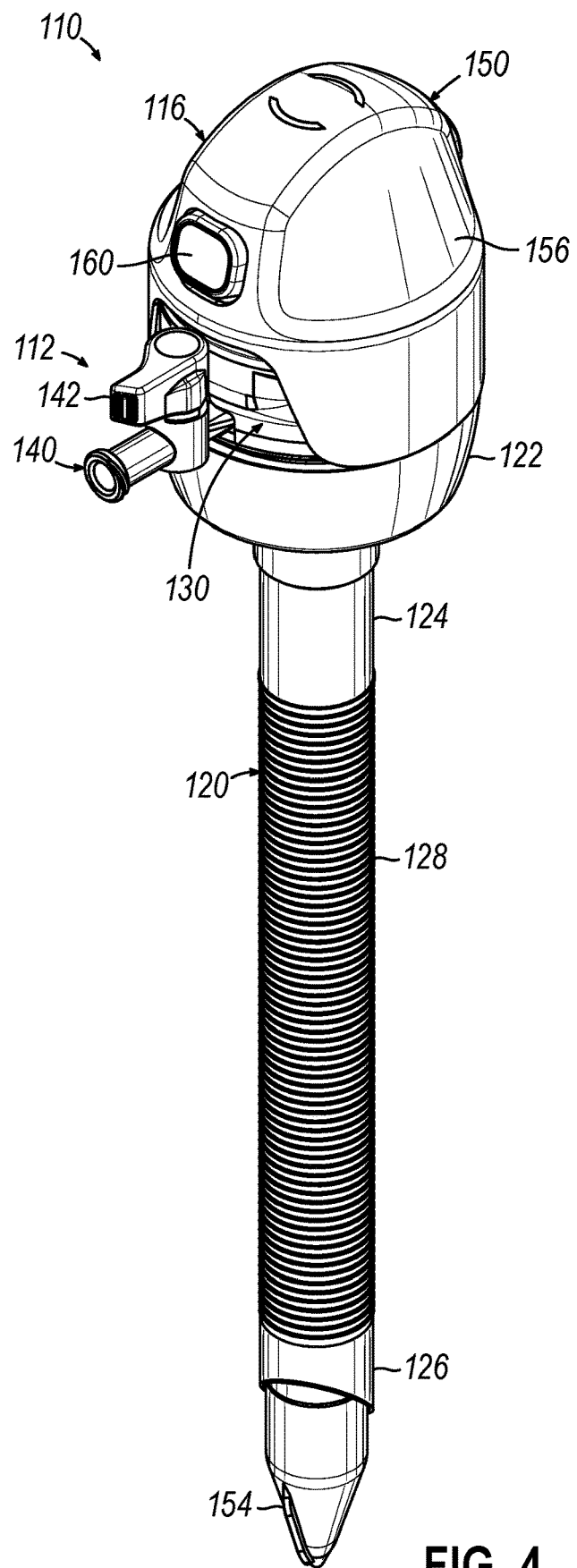
FIG. 4 depicts a perspective view of another exemplary trocar having a cannula assembly and an obturator shown in an assembled state, where the cannula assembly includes a cannula tube.
Figure 5:
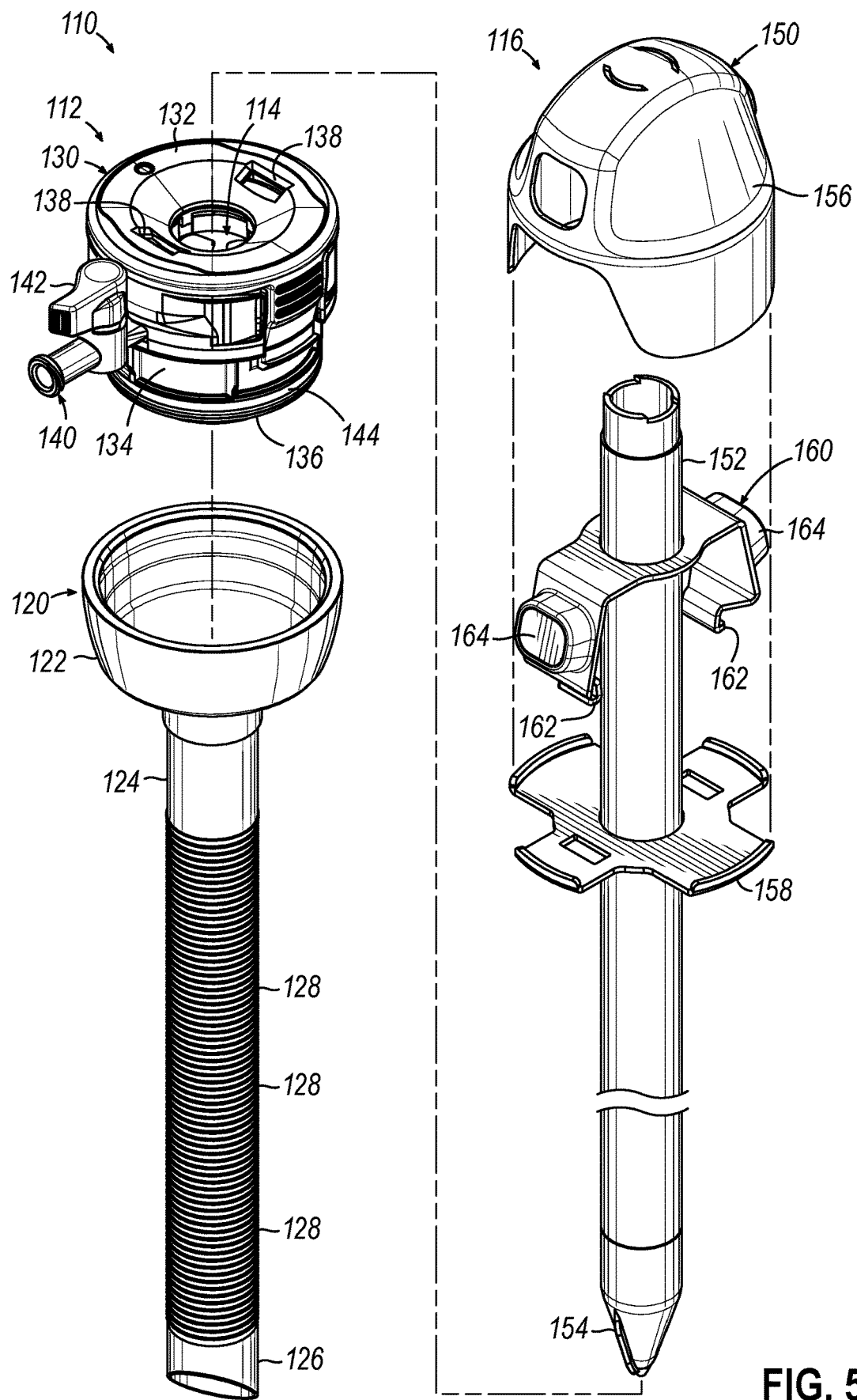
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with an opening of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. EXEMPLARY DEPTH LIMITERS

In some instances, a clinician may desire to limit the depth to which a single-use or reusable trocar (10, 110) may travel into abdominal wall (2) (e.g., after insertion of trocar (10, 110) to a desired position). Limiting the depth to which trocar (10, 110) may travel into abdominal wall (2) may assist in preventing distal tip (64, 154) of obturator (16, 116) and/or cannula tip (24, 126) of cannula assembly (12, 112) from inadvertently entering deeper than desired into abdominal cavity (1). Preventing over insertion of trocar (10, 110) may reduce undesirable contact of distal tip (64, 154) and/or cannula tip (24, 126) with anatomical structures contained within abdominal cavity (1).

Alternatively or in addition to limiting the depth to which single-use or reusable trocar (10, 110) may travel into abdominal wall (2), the clinician may desire to stabilize trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tip (24, 126), and thus, the entry point of surgical instruments into abdominal cavity (1)) in a desired position and/or orientation relative to abdominal cavity (1).

As described above with reference to FIGS. 1-5, obturators (16, 116) are configured to be removably coupled with cannulas (20, 120) along a central axis (shown as trocar central axis (A) in FIGS. 1-2) to facilitate insertion of the surgical access device through a body cavity wall (shown as abdominal wall (2)) of the patient. Cannulas (20, 120) include working channels (14, 114) and tissue gripping features (shown as ribs 26, 128). Working channels (14, 114) are configured to guide a surgical instrument (not shown) along a central axis of cannulas (20, 120). Tissue gripping features are intended to include non-helical features (e.g., such as ridges and annular scallops) as well as helical threads (e.g., overlapping or non-overlapping threads). The tissue gripping features may extend along only a portion of the length of cannula tube (124). As previously described, ribs (26, 128) are formed as annular scallops. Ribs (26, 128) may disposed along an outer surface of cannula (20, 120). As shown in FIGS. 3A-3D, ribs (26, 128) may be configured to stabilize cannula (20, 120) relative to abdominal wall (2) of the patient when cannula (20, 120) is inserted distally through abdominal wall (2).

To reduce over insertion and/or under insertion or trocar (10, 110), exemplary depth limiters (210, 310, 410, 1010, 1110, 1210, 1310, 1410) may be selectively coupled with cannula tube (22, 124, 216, 218, 316, 318) of cannula (20, 120, 212, 214, 312, 314). Depth limiters (210, 310, 410, 1010, 1110, 1210, 1310, 1410) are described in detail below with reference to FIGS. 6-20, and may be use alone or in combination with another depth limiter (210, 310, 410, 1010, 1110, 1210, 1310, 1410) if desired. For example, depth limiters (210, 310, 410) may securely retain cannulas, including but not limited to, cannulas having a 5 mm diameter, an 8 mm diameter, a 10 mm diameter, and a 12 mm diameter. Depth limiters (1010, 1110, 1210, 1310, 1410) may be scaled to fit a variety of different sized cannula tubes, including but not limited to, cannulas having a 5 mm diameter, an 8 mm diameter, a 10 mm diameter, and a 12 mm diameter.

Depth limiter (210) is shown in relation to trocar (110) of FIGS. 4-5 and cannula tubes (124, 216, 218) of cannulas (120, 212, 214). Depth limiter (310) is shown in relation to cannula tubes (124, 216, 218) of cannulas (120, 212, 214). Additionally, depth limiters (1010, 1110, 1210) are shown with relation to trocar (10), cannula (20), and cannula tube (22) of FIGS. 1-3. Depth limiters (1310, 1410) are shown with relation to trocar (110) of FIGS. 4-5. However, it is envisioned that depth limiters (210, 310, 410, 1010, 1110, 1210, 1310, 1410) may be used with a variety of other trocars, cannula assemblies, and obturators, including trocars (10, 110) and cannula tubes (22, 124, 216, 218, 316, 318) of cannulas (20, 120, 212, 214, 312, 314).

A. First Exemplary Depth Limiter

Figure 6:
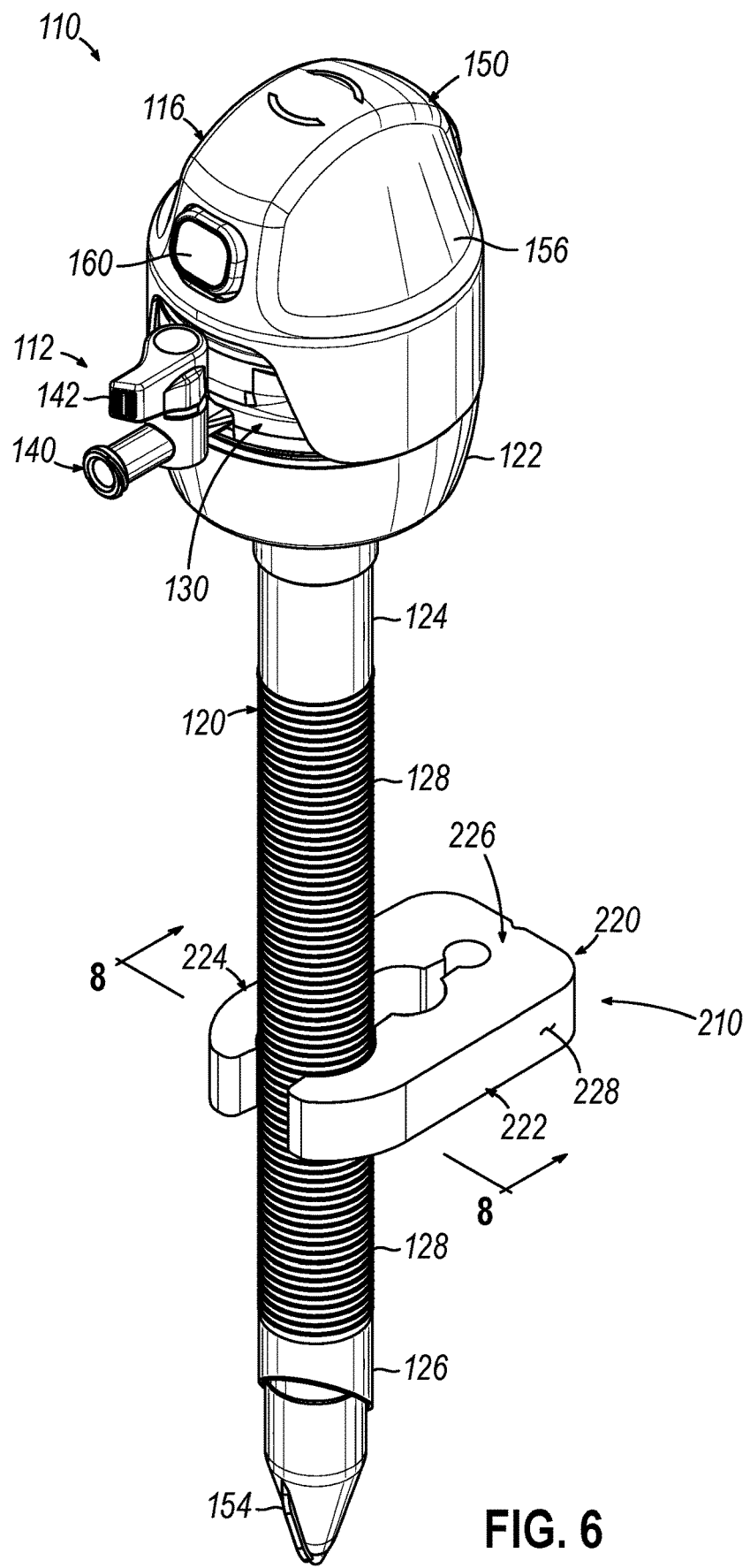
FIG. 6 depicts a perspective view of the trocar of FIG. 4 and a first exemplary depth limiter, where the depth limiter is in a closed configuration that restricts axial movement of the depth limiter relative to the cannula tube of the cannula assembly of the trocar.

FIGS. 6-9E show a first exemplary depth limiter (210) with relation to a surgical access device (shown as trocar (110)), which includes cannula assembly (112) and obturator (116) as described above. Depth limiter (210) is movable between an open configuration (see FIG. 9A) and a closed configuration (see FIGS. 9B-9E). Particularly, FIG. 6 shows a perspective view of trocar (110) of FIG. 4, where depth limiter (210) is in the closed configuration that restricts axial movement along a longitudinal axis (A1) of depth limiter (210) relative to cannula tube (124) of cannula assembly (112).

Figure 7:
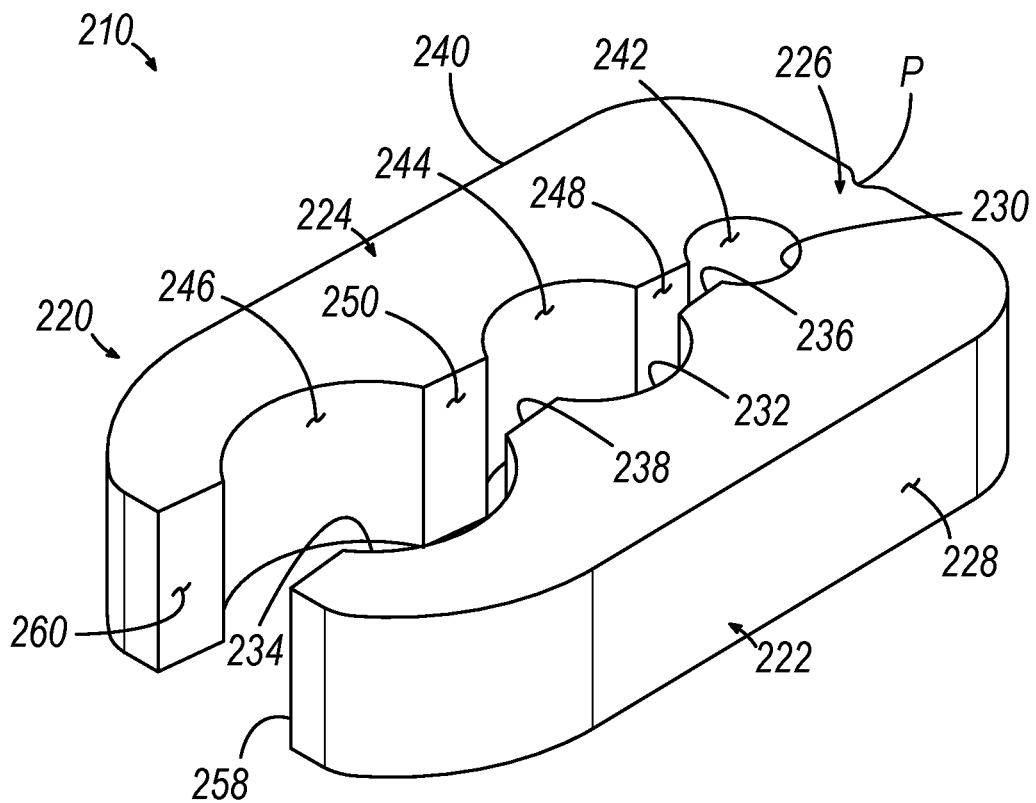
FIG. 7 depicts a perspective view of the depth limiter of FIG. 6.

FIG. 7 shows a perspective view of depth limiter (210) of FIG. 6. As shown, depth limiter (210) includes a housing (220). Housing (220) may be longer and/or wider to provide additional stability to depth limiter (210). Housing (220) may include body portions (shown as arms (222, 224)) and a flexible hinge (shown as a living hinge (226)). As shown, living hinge (226) is disposed between arms (222, 224). Arms (222, 224) may be pivotably coupled together at a pivot point (P) using living hinge (226) between the open and closed configurations. Living hinge (226) may provide the desired clamp force onto the outer diameter of cannula tube (124, 216, 218). Depth limiter (210) may couple with engagement features (e.g., ribs (128)) of cannula tube (124, 216, 218). Depth limiter (210) may be used repeatedly during a surgery.

Arm (222) may include a user contact portion (shown as outer surface (228)) and gripping surfaces (230, 232, 234).

Gripping surface (230) of arm (222) may be spaced apart from gripping surface (232) of arm (222) by a connecting portion (236), and gripping surface (232) of arm (222) may be spaced apart from gripping surface (234) of arm (222) by a connecting portion (238). Similarly, arm (224) may include a user contact portion (shown as outer surface (240)) and gripping surfaces (242, 244, 246). Gripping surface (242) of arm (224) may be spaced apart from gripping surface (244) of arm (224) by a connecting portion (248), and gripping surface (244) of arm (224) may be spaced apart from gripping surface (246) of arm (224) by a connecting portion (250). Similarly, a connecting portion (258) may be disposed between gripping surface (234) and outer surface (228) of arm (222), and a connecting portion (260) may be disposed between gripping surface (246) and outer surface (240) of arm (224). While not shown, at least one of outer surfaces (228, 240) may include a textured surface for enhanced gripping by the user.

Figure 8:
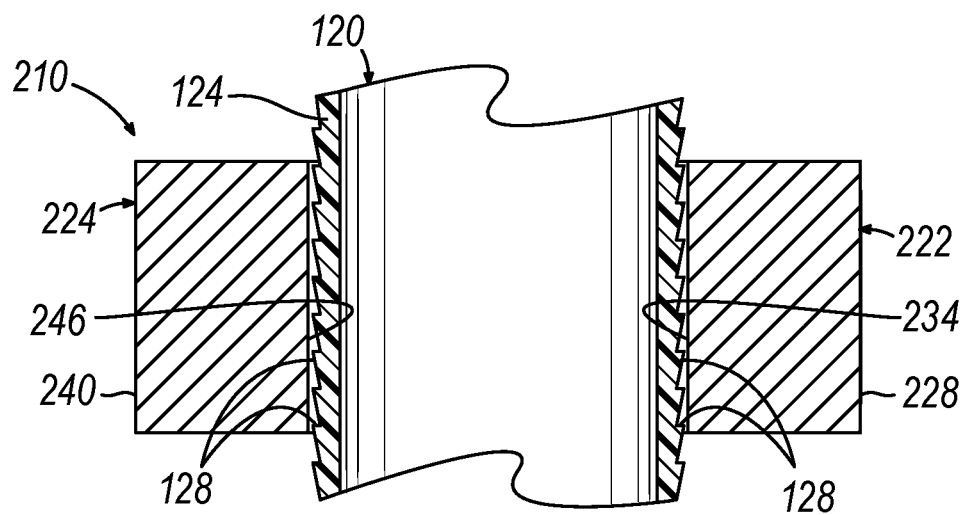
FIG. 8 depicts a cross-sectional view of the depth limiter and the cannula tube of FIG. 6 taken along line 8-8 of FIG. 6.

FIG. 8 shows a cross-sectional view of depth limiter (210) and cannula tube (124) of FIG. 6 taken along line 8-8 of FIG. 6. Gripping surfaces (230, 232, 234, 242, 244, 246) may be smooth, non-smooth, or a combination of smooth and non-smooth. As shown, gripping surfaces of arms (222, 224) are both smooth and may be configured to frictionally engage with engagement features (e.g., ribs (128)) of cannula tube (124) of cannula (120) in the closed configuration, and not frictionally engage ribs (128) of cannula (120) in the open configuration.

A non-smooth surface on one or more of gripping surfaces (230, 232, 234, 242, 244, 246) may include one or more features to lockingly engage cannula tube (124). While not shown, at least one gripping surface (230, 232, 234, 242, 244, 246) of arms (222, 224) may include engagement features (e.g., ridges) to lockingly engage with tissue gripping features (e.g., ribs (128)) disposed along an outer surface of cannula tube (124, 216, 218) in the closed configuration, and not lockingly engage with rib (128) of cannula (120) in the open configuration. Depth limiter (210) may use the engagement features of cannula tube (124, 216, 218) to counter the normal force imparted when depth limiter (210) contacts the body wall (e.g., abdominal wall (2)). Engagement features (e.g., ridges) may intimately mate with ribs (128)) of cannula tube (124, 216, 218) to facilitate force transfer. Gripping surfaces (230, 232, 234, 242, 244, 246) are shown to be arcuate and continuous; however, gripping surfaces (230, 232, 234, 242, 244, 246) may vary in shape.

Figure 9A:
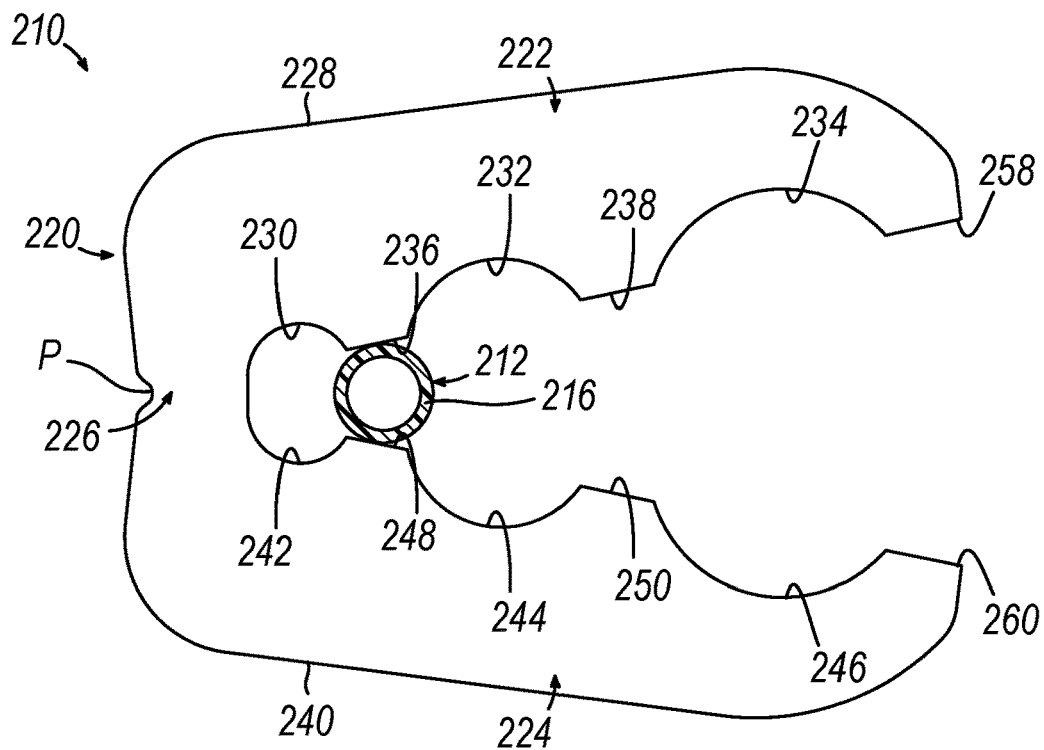
FIG. 9A depicts a top plan view of the depth limiter of FIG. 7 and an exemplary cannula tube shown in cross-section, with the depth limiter in an open configuration allowing for axial movement of the depth limiter relative to the cannula tube when actuated by a user.

FIGS. 9A-9E show depth limiter (210) accepting and coupling with discrete cannula tubes having various diameters. For example, arms (222, 224) may be pivotably coupled together using living hinge (226) between the open configuration configured to receive cannula tubes (124, 216, 218) of cannulas (120, 212, 214) and the closed configuration configured to couple with cannula tubes (124, 216, 218) of cannulas (120, 212, 214). FIG. 9A shows depth limiter (210) in the open configuration, and FIGS. 9B-9E show depth limiter (210) in the closed configuration.

FIG. 9A shows a top plan view of depth limiter (210) of FIG. 7 and cannula tube (216) of cannula (212) being shown in cross-section. In the open configuration, depth limiter (210) may allow for axial movement of depth limiter (210) relative to cannula tubes (124, 216, 218) of cannulas (120, 212, 214). For example, a user may pinch two points to increase the effective diameter between opposing gripping surface (230, 242), between opposing gripping surfaces (232, 244), and between opposing gripping surfaces (234, 246). As shown, outer surfaces (228, 240) are configured to be actuated by the user using thumb and index fingers. However, the user may depress outer surfaces (228, 240) in other ways (e.g., using one or more fingers and the palm). In FIG. 9A, cannula tube (216) of cannula (212) is shown passing through connecting portion of (236) of arm (222) and connecting portion (248) of arm (224). As shown, cannula tube (216) of cannula (212) already passed through connecting portions (238, 258) of arm (222) and connecting portions (250, 260) of arm (224).

Figure 9B:
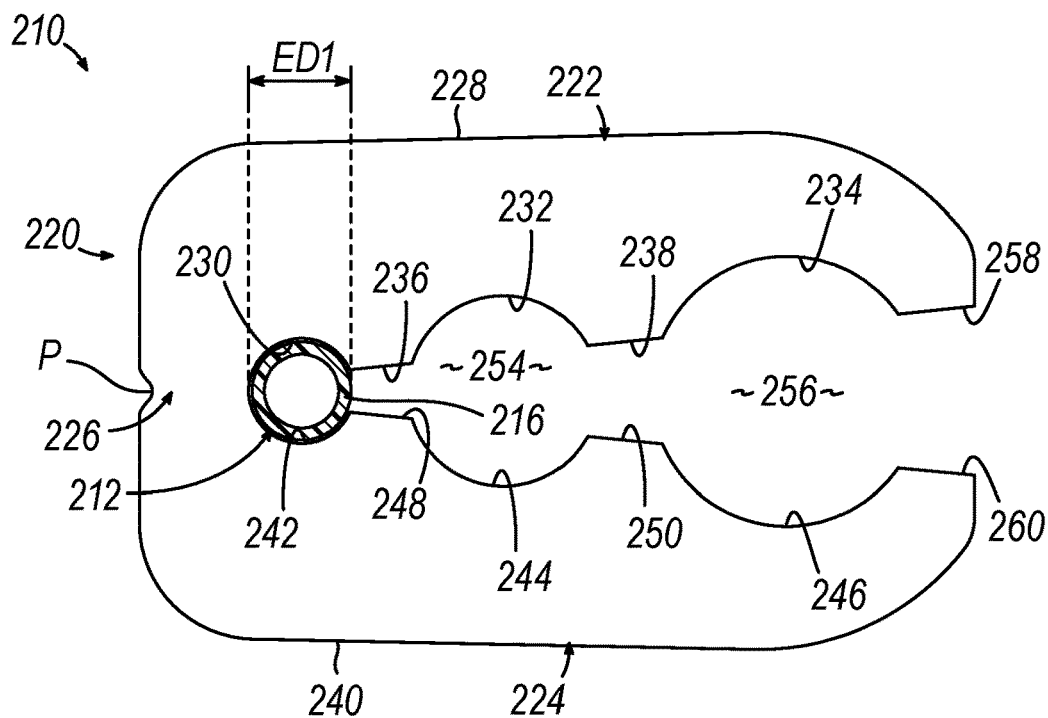
FIG. 9B depicts a top plan view of the depth limiter and the cannula tube of FIG. 9A, but with the depth limiter in the closed configuration.

FIG. 9B shows a top plan view of depth limiter (210) and cannula tube (216) of cannula (212) of FIG. 9A, but with depth limiter (210) in the closed configuration. Once the desired cannula tube (124, 216, 218) of cannula (120, 212, 214) is aligned, the user may release outer surfaces (228, 240) to decrease the effective diameter between opposing gripping surface (230, 242), between opposing gripping surfaces (232, 244), and between opposing gripping surfaces (234, 246). This transitions depth limiter (210) to the closed configuration, where depth limiter (210) is fixed (e.g., clamped) to cannula tube (216). Gripping surface (242) of arm (224) together with gripping surface (230) of arm (222) collectively form an opening (252) having a first effective diameter (ED1) that is configured to selectively couple with cannula tube (216) of cannula (212). In the closed configuration, gripping surface (230) of arm (222) is spaced apart by a gap from gripping surface (242) of arm (224). Arms (222, 224) may be inwardly biased to capture cannula tube (216) when compared to FIG. 9E.

Figure 9C:
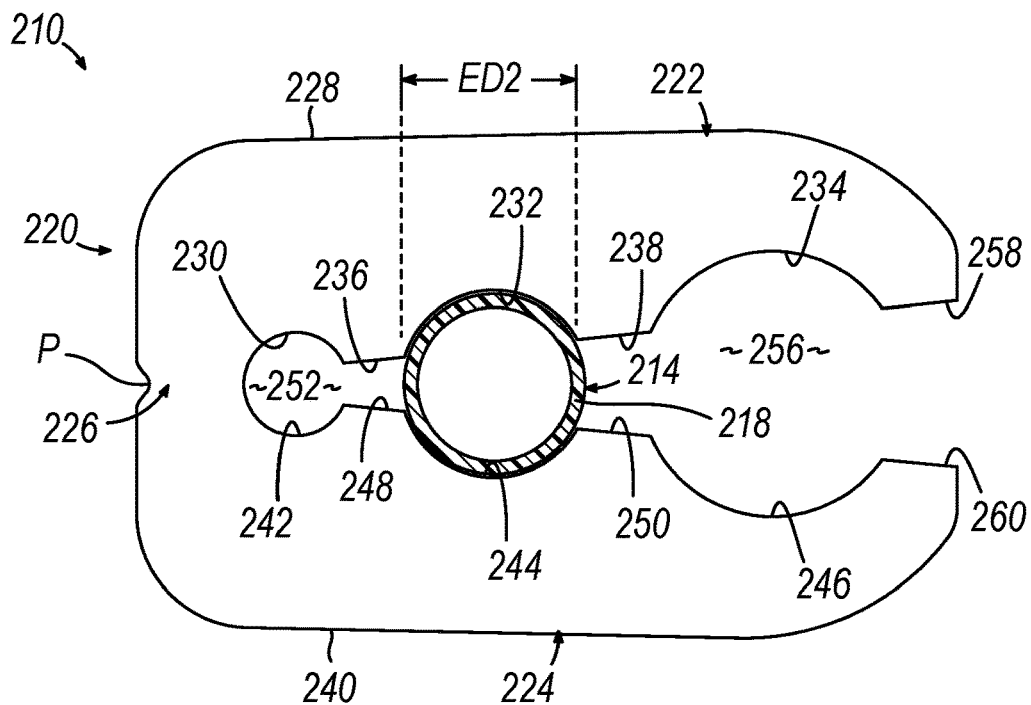
FIG. 9C depicts a top plan view of the depth limiter of FIG. 9A and another exemplary cannula tube, where the depth limiter is in the closed configuration.

FIG. 9C shows a top plan view of depth limiter (210) of FIG. 9A and cannula tube (218) of cannula (214), where depth limiter is (210) in the closed configuration. Gripping surface (244) of arm (224) together with gripping surface (232) of arm (222) collectively form an opening (254) having a second effective diameter (ED2) that is configured to selectively couple with cannula tube (218) of cannula (214). Second effective diameter (ED2) is greater than first effective diameter (ED1). Arms (222, 224) may be inwardly biased to capture cannula tube (218) when compared to FIG. 9E.

Figure 9D:
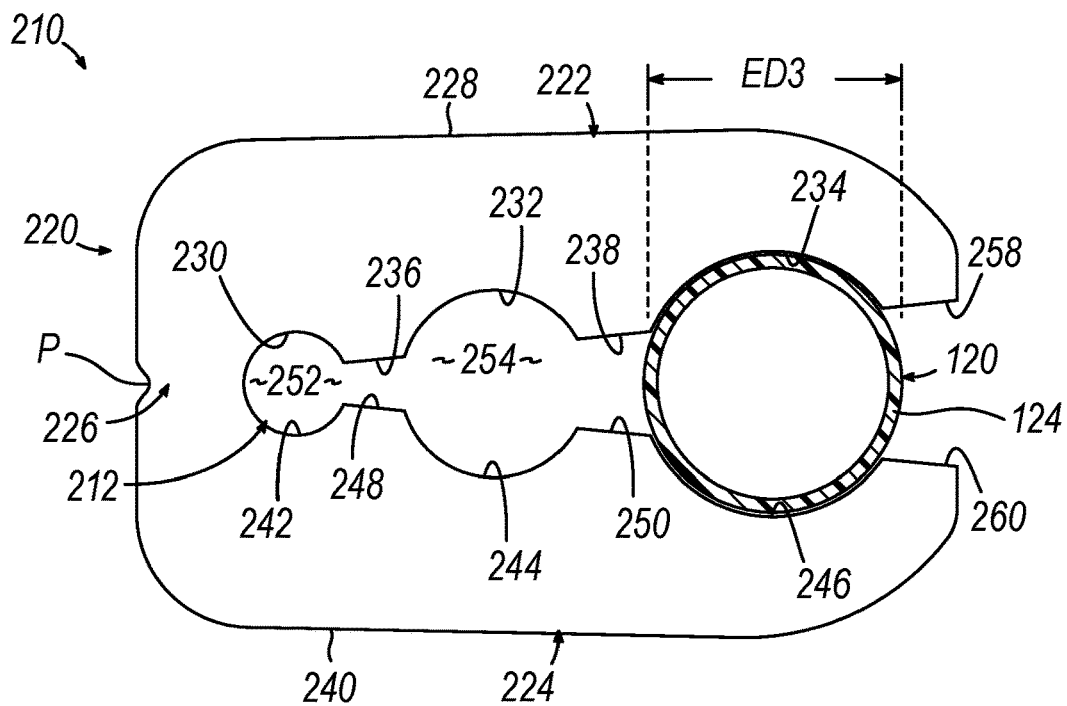
FIG. 9D depicts a top plan view of the depth limiter of FIG. 9A and the cannula tube of FIG. 5, where the depth limiter is in the closed configuration.
Figure 9E:
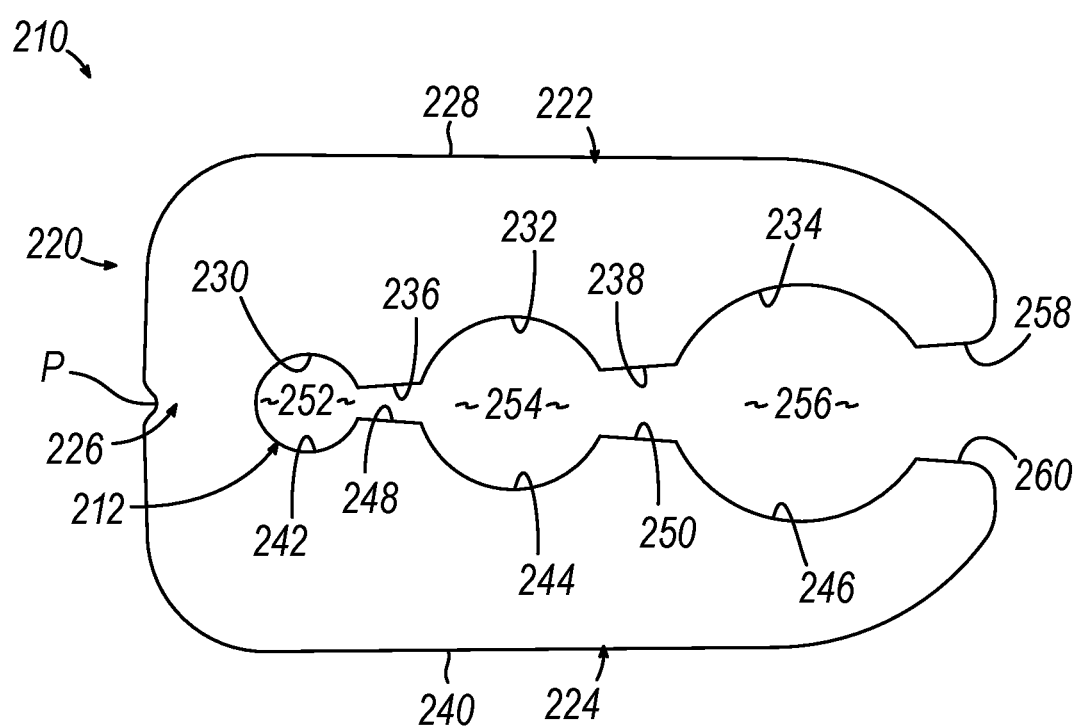
FIG. 9E depicts a top plan view of the depth limiter of FIG. 9A in the closed configuration.

FIG. 9D shows a top plan view of depth limiter (210) of FIG. 9A and cannula tube (124) of FIG. 5, where depth limiter (210) is in the closed configuration. Gripping surface (246) of arm (224) together with gripping surface (234) of arm (222) collectively form an opening (256) having a third effective diameter (ED3) that is configured to selectively couple with cannula tube (124) of cannula (120). The third effective diameter (ED3) is be greater than either of first and second effective diameters (ED1, ED2). As shown, openings (252, 254, 256) are separate and discrete from one another. Arms (222, 224) are biased inwardly when compared to the resting configuration of FIG. 9E. As shown in FIGS. 9B-9D, in fixed configuration, depth limiter (210) is configured to restrict axial movement of depth limiter (210) relative to cannula tubes (124, 216, 218) of cannulas (120, 212, 214). For example, first effective diameter (ED1) may be approximately 5 millimeters, where second effective diameter (ED2) may be approximately 10 millimeters, and where third effective diameter (ED3) may be approximately 12 millimeters.

Depth limiter (210) may be reusable or disposable. In some versions, arms (222, 224) and living hinge are integrally formed together as a unitary piece. Depth limiter may be formed entirely of a polymeric material. Depth limiter (210) may be injection molded for a disposable model. Alternatively, depth limiter (210) may be and stamped, machined, and/or metal-injection molded for a re-usable model. In some versions, depth limiter (210) is completely formed of metal. Depth limiter (210) may include simple to operate pinch-to release controls.

B. Second Exemplary Depth Limiter

Figure 10:
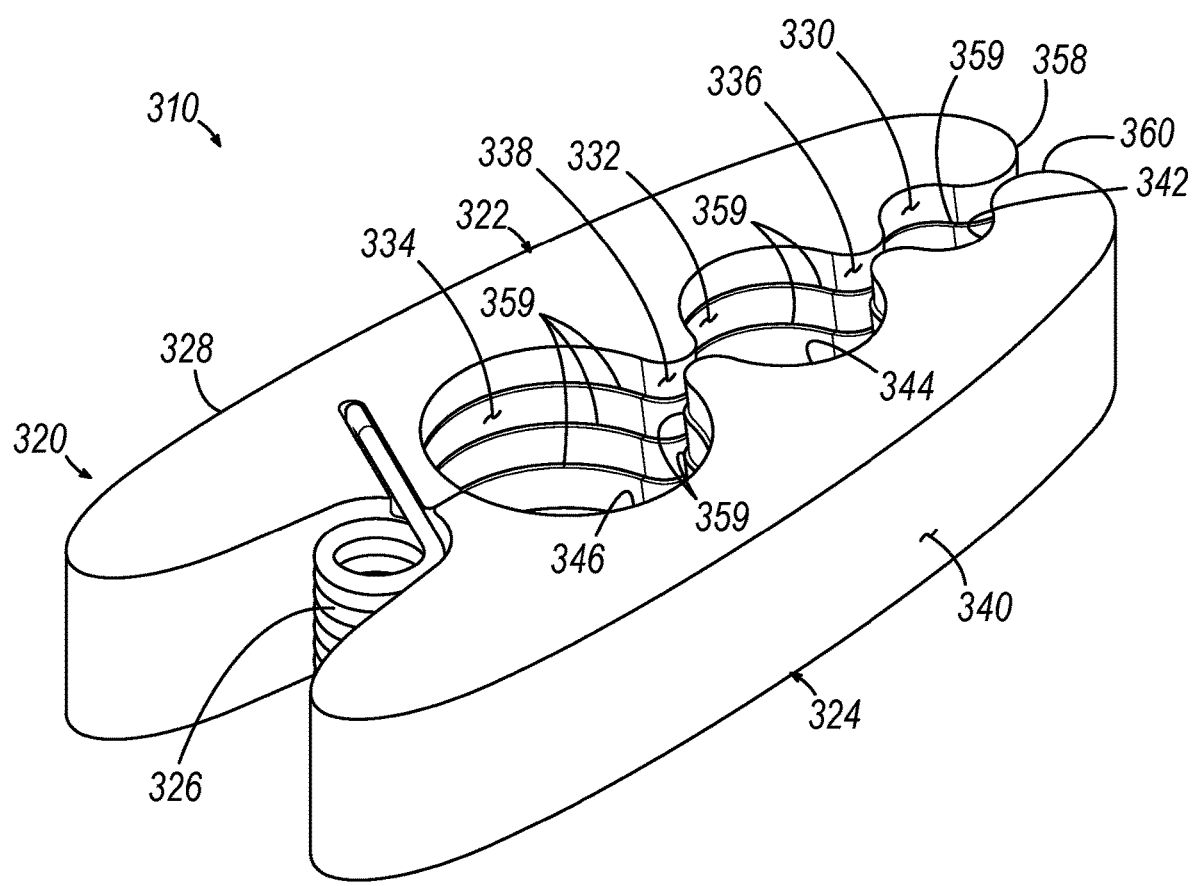
FIG. 10 depicts a perspective view of a second exemplary depth limiter.
Figure 11A:
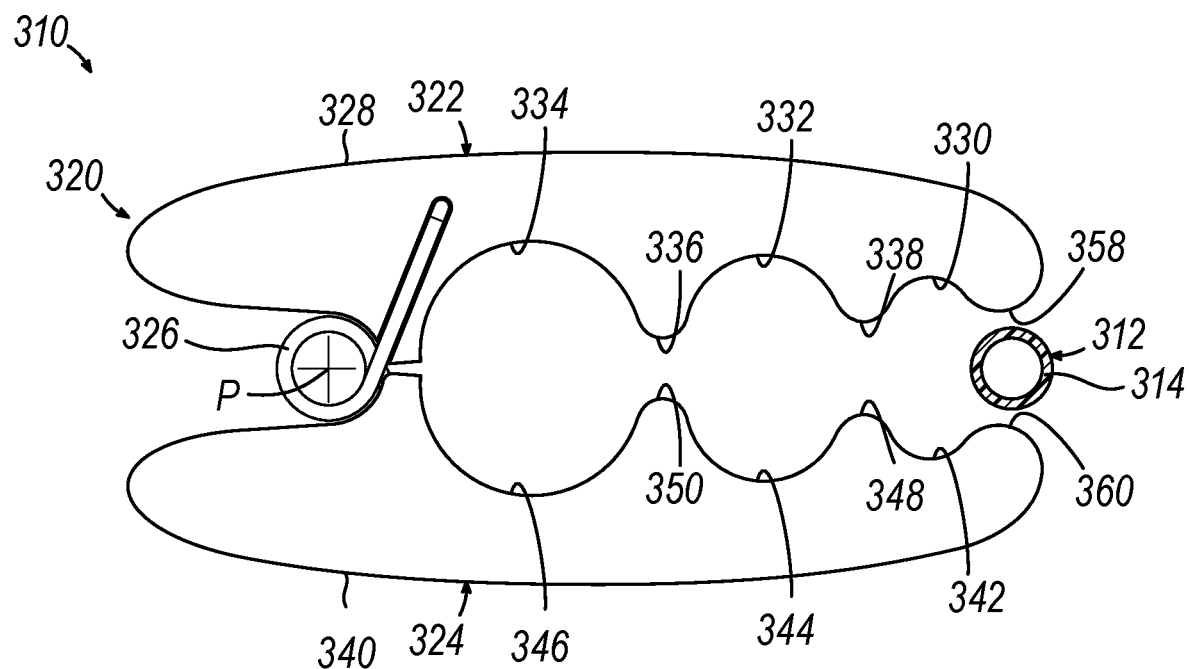
FIG. 11A depicts a top plan view of the depth limiter of FIG. 10 coupled with an exemplary cannula tube, where the depth limiter is in an open configuration allowing for axial movement of the depth limiter relative to the cannula tube when actuated by a user.
Figure 11B:
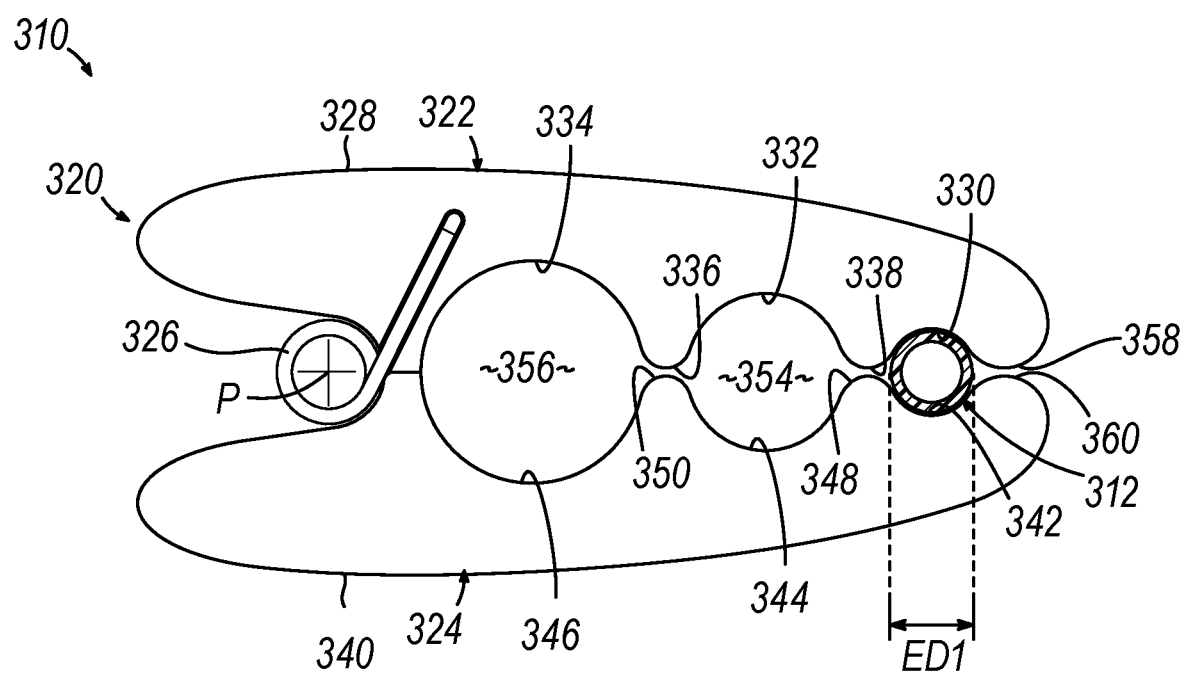
FIG. 11B depicts a top plan view of the depth limiter and cannula tube of FIG. 11A, but with the depth limiter in a closed configuration that restricts axial movement of the depth limiter relative to the cannula tube.
Figure 11C:
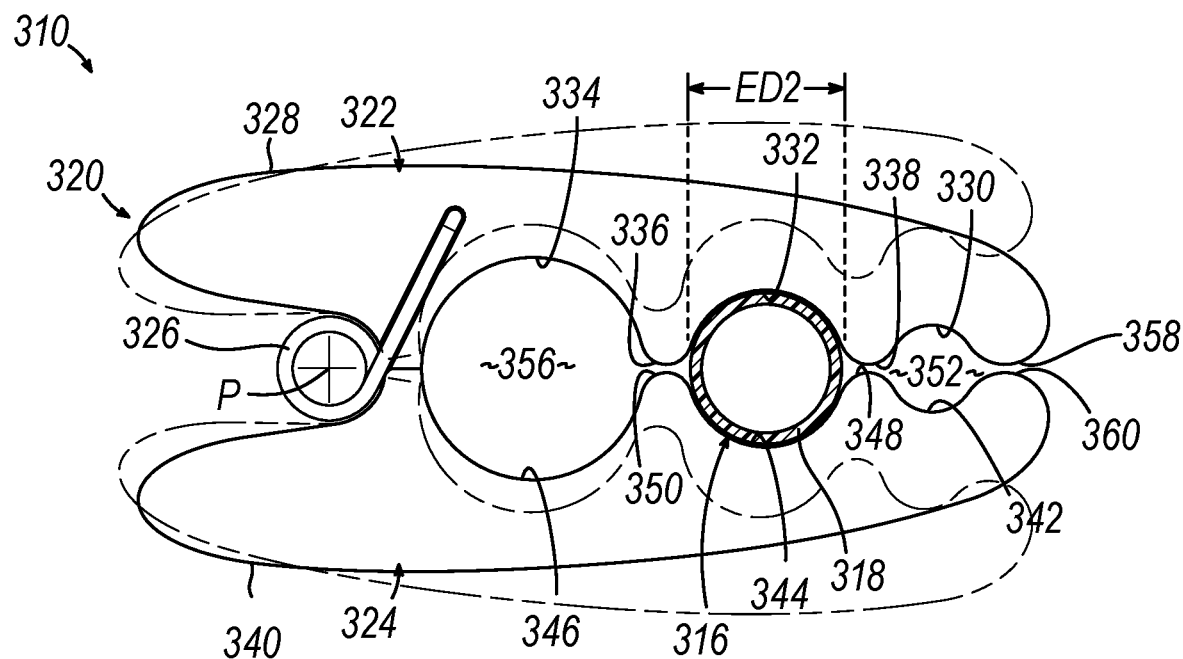
FIG. 11C depicts a top plan view of the depth limiter of FIG. 11A and another exemplary cannula tube, where the depth limiter is in the closed configuration that restricts axial movement of the depth limiter relative to the cannula tube and the open configuration being shown in phantom.
Figure 11D:
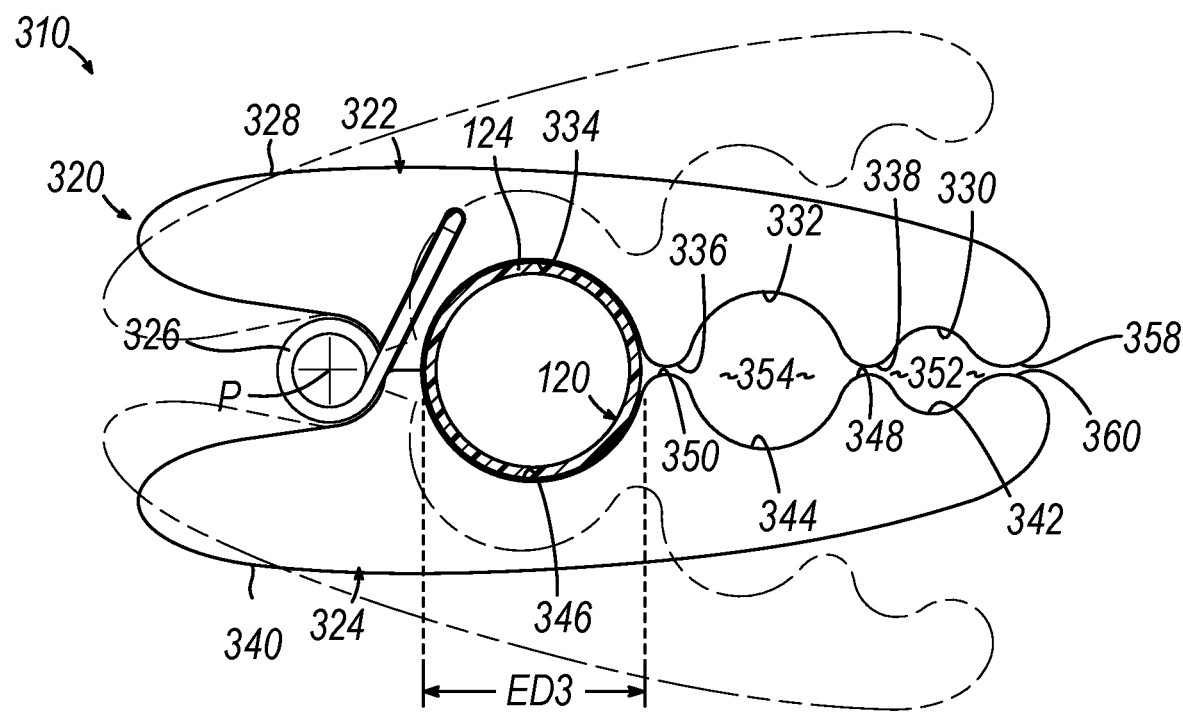
FIG. 11D depicts a top plan view of the depth limiter of FIG. 11A and the cannula tube of FIG. 5, where the depth limiter is in the closed configuration that restricts axial movement of the depth limiter relative to the cannula tube and the open configuration being shown in phantom.

FIGS. 10-11D show a second exemplary depth limiter (310) with relation to a surgical access device (e.g., trocar 10, 110). Particularly FIG. 10 shows a perspective view of depth limiter (310) that is movable between an open configuration and a closed configuration. As shown, depth limiter (310) includes a housing (320). Housing (320) may be longer and/or wider to provide additional stability to the surgical access device. Housing (320) may include body portions (shown as arms (322, 324)) and a biasing feature (shown as a torsion spring (326)). Another suitable spring is also envisioned, including but not limited to, a leaf spring. As shown, torsion spring (326) is disposed between arms (322, 324). Torsion spring (326) may be fixably attached to arms (322, 324) using a friction fit and/or an adhesive. Arms (322, 324) may be pivotably coupled together at a pivot point (P) using torsion spring (326) between the open and closed configurations. As shown, arms (322, 324) are separate and distinct; however, arms (322, 324) may be connected. Torsion spring (326) may provide the desired clamp force onto the outer diameter of cannula tube (124, 316, 318). While not shown, depth limiter (310) may include a living hinge, similar to living hinge (226). Depth limiter (310) may couple with cannula tubes having different diameters (e.g., cannula tubes (124, 316, 318)). Depth limiter (310) may be transitioned between the closed and open configurations repeatedly during a surgery. Cannula tube (316) may be sized similar to cannula tube (216), and cannula tube (318) may be sized similar to cannula tube (218)

Arm (322) may include a user contact portion (shown as outer surface (328)) and gripping surfaces (330, 332, 334). Gripping surface (330) of arm (322) may be spaced apart from gripping surface (332) of arm (322) by a connecting portion (336), and gripping surface (332) of arm (322) may be spaced apart from gripping surface (334) of arm (322) by a connecting portion (338). Similarly, arm (324) may include a user contact portion (shown as outer surface (340)) and gripping surfaces (342, 344, 346). Gripping surface (342) of arm (324) may be spaced apart from gripping surface (344) of arm (324) by a connecting portion (348), and gripping surface (344) of arm (324) may be spaced apart from gripping surface (346) of arm (324) by a connecting portion (350). Similarly, a connecting portion (358) may be disposed between gripping surface (330) and outer surface (328) of arm (322), and a connecting portion (360) may be disposed between gripping surface (342) and outer surface (340) of arm (324). While not shown, at least one of outer surfaces (328, 340) may include a textured surface for enhanced gripping by the user.

Gripping surfaces (330, 332, 334, 342, 344, 346) may be smooth, non-smooth, or a combination of smooth and non-smooth. A non-smooth surface may include one or more features to lockingly engage cannula tube (124, 316, 318). For example, at least one of gripping surfaces of arms (322, 324) may include engagement features (shown as ridges (359)) to lockingly engage with tissue gripping features (e.g., ribs (128)) disposed along an outer surface of cannula tube (124, 316, 318) in the closed configuration, and not lockingly engage with rib (128) of cannula (120) in the open configuration. Depth limiter (310) may use the engagement features of cannula tube (124, 316, 318) to counter the normal force imparted when depth limiter (310) contacts the body wall (e.g., abdominal wall (2)). Engagement features (shown as ridges (359)) may intimately mate with ribs (128)) of cannula tube (124, 316, 318) to facilitate force transfer. Gripping surfaces (330, 332, 334, 342, 344, 346) are shown to be arcuate and continuous; however, gripping surfaces (330, 332, 334, 342, 344, 346) may vary. While not shown, gripping surfaces of arms (322, 324) may be smooth and configured to frictionally engage with engagement features (e.g., ribs (128)) of cannula tube (124, 316, 318) of cannula (120, 312, 314) in the closed configuration, and not frictionally engage ribs (128) of cannula (120) in the open configuration.

FIGS. 11A-11D show how depth limiter (310) may accept and couple with cannula tubes having different diameters. Arms (322, 324) may be pivotably coupled together using torsion spring (326) between the open configuration configured to receive cannula tubes (124, 316, 318) of cannulas (120, 312, 314) and the closed configuration configured to couple with cannula tubes (124, 316, 318) of cannulas (120, 312, 314). FIG. 11A shows a top plan view of depth limiter (310) of FIG. 10 and cannula tube (316) of cannula (312) being shown in cross-section. In the open configuration, depth limiter (310) may allow for axial movement of depth limiter (310) relative to cannula tubes (124, 316, 318) of cannulas (120, 312, 314). For example, a user may pinch two points to increase the effective diameter between opposing gripping surface (330, 342), between opposing gripping surfaces (332, 344), and between opposing gripping surfaces (334, 346). As shown, outer surfaces (328, 340) are configured to be actuated by the user using thumb and index fingers. However, the user may depress outer surfaces (328, 340) in other ways (e.g., using one or more fingers and the palm).

FIG. 11B shows a top plan view of depth limiter (310) and cannula tube (316) of cannula (312) of FIG. 11A, but with depth limiter (310) in the closed configuration. Once the desired cannula tube (124, 316, 318) of cannula (120, 312, 314) is aligned, the user may release outer surfaces (328, 340) to decrease the effective diameter between opposing gripping surface (330, 342), between opposing gripping surfaces (332, 344), and between opposing gripping surfaces (334, 346). This transitions depth limiter (310) to the closed configuration, where depth limiter (310) is fixed (e.g., clamped) to cannula tube (124, 316, 318). As shown in FIG. 11B, gripping surface (342) of arm (324) together with gripping surface (330) of arm (322) collectively form an opening (352) having a first effective diameter (ED1) that is configured to selectively couple with cannula tube (316) of cannula (312). In the closed configuration, gripping surface (330) of arm (322) may be spaced apart by a gap from gripping surface (342) of arm (324). Arms (322, 324) may be biased inwardly to capture and retain cannula tube (316) when compared to the resting configuration of FIG. 10.

FIG. 11C shows a top plan view of depth limiter (310) of FIG. 11A and cannula tube (318) of cannula (314), where depth limiter is (310) in the closed configuration. As shown, gripping surface (344) of arm (324) together with gripping surface (332) of arm (322) collectively form an opening (354) having a second effective diameter (ED2) that is configured to selectively couple with cannula tube (318) of cannula (314). Second effective diameter (ED2) is greater than first effective diameter (ED1). Arms (322, 324) may be biased inwardly to capture cannula tube (318) when compared to the resting configuration of FIG. 9E. Additionally, FIG. 11C shows the open configuration in phantom allowing for cannula tube (318) of cannula (314) to be inserted into and from opening (356).

FIG. 11D shows a top plan view of depth limiter (310) of FIG. 11A and cannula tube (124) of FIG. 5, where depth limiter (310) is in the closed configuration. Gripping surface (346) of arm (324) together with gripping surface (334) of arm (322) collectively form an opening (356) having a third effective diameter (ED3) that is configured to selectively couple with cannula tube (124) of cannula (120). The third effective diameter (ED3) may be greater than either of first and second effective diameters (ED1, ED2). Openings (352, 354, 356) are separate and discrete from one another. Arms (322, 324) may be biased inwardly when compared to the resting configuration of FIG. 10. Additionally, FIG. 11D shows the open configuration in phantom allowing for cannula tube (318) of cannula (314) to be inserted into and from opening (356).

As shown in FIGS. 11B-11D, in fixed configuration, depth limiter (310) is configured to restrict axial movement of depth limiter (310) relative to cannula tubes (124, 316, 318) of cannulas (120, 312, 314). For example, first effective diameter (ED1) may be approximately 5 millimeters, second effective diameter (ED2) may be approximately 10 millimeters, and third effective diameter (ED3) may be approximately 12 millimeters.

Depth limiter (310) may be reusable or disposable. Depth limiter may be formed entirely of a polymeric material. Depth limiter (310) may be injection molded for a disposable model. Alternatively, depth limiter (310) may be and stamped, machined, and/or metal-injection molded for a re-usable model. In some versions, depth limiter (310) is completely formed of metal. Depth limiter (310) may include simple to operate pinch-to release controls.

C. Third Exemplary Depth Limiter

Figure 12:
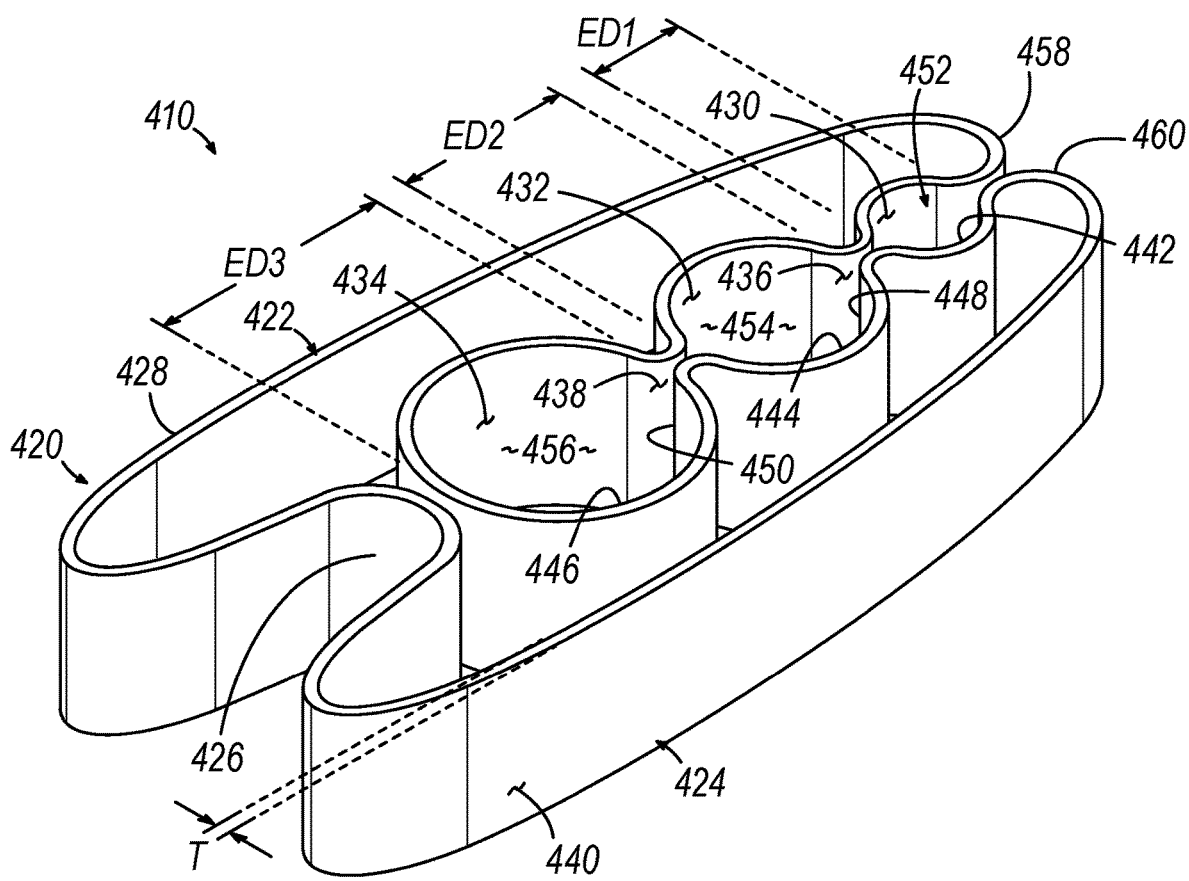
FIG. 12 depicts a perspective view of a third exemplary depth limiter.

FIG. 12 shows a third exemplary depth limiter (410) with relation to a surgical access device. Similar to depth limiters (210, 310), depth limiter (410) is movable between an open configuration and a closed configuration. As shown, depth limiter (410) includes a housing (420). Housing (420) may be integrally formed together as a unitary piece. In some versions, housing (420) may be a thin metal ribbon that is formed into the desired shape. The thickness (T) of housing (420) affects the force required to transition depth limiter (410) between the open and closed configurations. Housing (420) may be longer and/or wider to provide additional stability. A thin metal ribbon allows for housing (420) to be efficiently and effectively sterilized. Housing (420) may include body portions (shown as arms (422, 424)) and a living hinge (426). Living hinge (426) may provide the desired clamp force onto the outer diameter of cannula tube (124, 216, 218, 316, 318). Living hinge (426) may also have thickness (T). Depth limiter (210) may accommodate multiple cannula tubes (124, 216, 218) and may be repeatedly used during a surgery.

Similar to arms (222, 322), arm (422) may include a user contact portion (shown as outer surface (428)) and gripping surfaces (430, 432, 434). Gripping surface (430) of arm (422) may be spaced apart from gripping surface (432) of arm (422) by a connecting portion (436), and gripping surface (432) of arm (422) may be spaced apart from gripping surface (434) of arm (422) by a connecting portion (438). Similar to arms (224, 324), arm (424) may include a user contact portion (shown as outer surface (440)) and gripping surfaces (442, 444, 446). Gripping surface (442) of arm (424) may be spaced apart from gripping surface (444) of arm (424) by a connecting portion (448), and gripping surface (444) of arm (424) may be spaced apart from gripping surface (446) of arm (424) by a connecting portion (450). Similarly, a connecting portion (458) may be disposed between gripping surface (430) and outer surface (428) of arm (422), and a connecting portion (460) may be disposed between gripping surface (442) and outer surface (440) of arm (424).

Gripping surfaces (430, 432, 434, 442, 444, 446) may be smooth, non-smooth, or a combination of smooth and non-smooth. As shown, gripping surfaces of arms (422, 424) are smooth and may be configured to frictionally engage with engagement features (e.g., ribs (128)) of cannula tube (124, 216, 218, 316, 318) of cannula (120, 412, 414) in the closed configuration, and not frictionally engage ribs (128) of cannula (120) in the open configuration. A non-smooth surface may include one or more features to lockingly engage cannula tube (124). While not shown, at least one of gripping surfaces of arms (422, 424) may include engagement features (e.g., ridges similar to ridges (359)) to lockingly engage with tissue gripping features (e.g., ribs (128)) disposed along an outer surface of cannula tube (124, 216, 218, 316, 318) in the closed configuration, and not lockingly engage with rib (128) of cannula (120) in the open configuration. Gripping surfaces (430, 432, 434, 442, 444, 446) are shown to be arcuate and continuous; however, gripping surfaces (430, 432, 434, 442, 444, 446) may vary.

Similar to depth limiter (210) with reference to FIGS. 9A-9E and depth limiter (310) with reference to FIGS. 11A-11D, a user may pinch two points to increase the effective diameter between opposing gripping surface (430, 442), between opposing gripping surfaces (432, 444), and between opposing gripping surfaces (434, 446). As shown, outer surfaces (428, 440) are configured to be actuated by the user using thumb and index fingers. However, the user may depress outer surfaces (428, 440) in other ways (e.g., using one or more fingers and the palm). Once the desired cannula tube (124, 216, 218, 316, 318) of cannula (120, 412, 414) is aligned, the user may release outer surfaces (428, 440) to decrease the effective diameter between opposing gripping surface (430, 442), between opposing gripping surfaces (432, 444), and between opposing gripping surfaces (434, 446). This transitions depth limiter (410) to the closed configuration, where depth limiter (410) is fixed (e.g., clamped) to cannula tube (124, 216, 218, 316, 318).

Gripping surface (442) of arm (424) together with gripping surface (430) of arm (422) collectively form an opening (452) having a first effective diameter (ED1) that is configured to selectively couple with cannula tube (416) of cannula (412). Similarly, gripping surface (444) of arm (424) together with gripping surface (432) of arm (422) collectively form an opening (454) having a second effective diameter (ED2) that is configured to selectively couple with cannula tube (418) of cannula (414). Second effective diameter (ED2) is greater than first effective diameter (ED1). Gripping surface (446) of arm (424) together with gripping surface (434) of arm (422) collectively form an opening (456) having a third effective diameter (ED3) that is configured to selectively couple with cannula tube (124) of cannula (120). The third effective diameter (ED3) may be greater than either of first and second effective diameters (ED1, ED2). Openings (452, 452, 456) are separate and discrete from one another. In fixed configuration, depth limiter (410) is configured to restrict axial movement of depth limiter (410) relative to cannula tubes (124, 216, 218, 316, 318) of cannulas (120, 412, 414). For example, first effective diameter (ED1) may be approximately 5 millimeters, where second effective diameter (ED2) may be approximately 10 millimeters, and where third effective diameter (ED3) may be approximately 12 millimeters.

Depth limiter (410) may be reusable or disposable. Depth limiter may be formed entirely of a polymeric material. Depth limiter (410) may be injection molded for a disposable model. Alternatively, depth limiter (410) may be and stamped, machined, and/or metal-injection molded for a re-usable model. In some versions, depth limiter (410) is completely formed of metal. Depth limiter (410) may made of a singular piece, where the spring like properties of metal allow depth limiter (410) to move between the fixed and open configurations without including a separate biasing feature (e.g., a leaf spring or a torsion spring). Depth limiter (410) may include simple to operate pinch-to release controls.

D. Fourth Exemplary Depth Limiter

Figure 13:
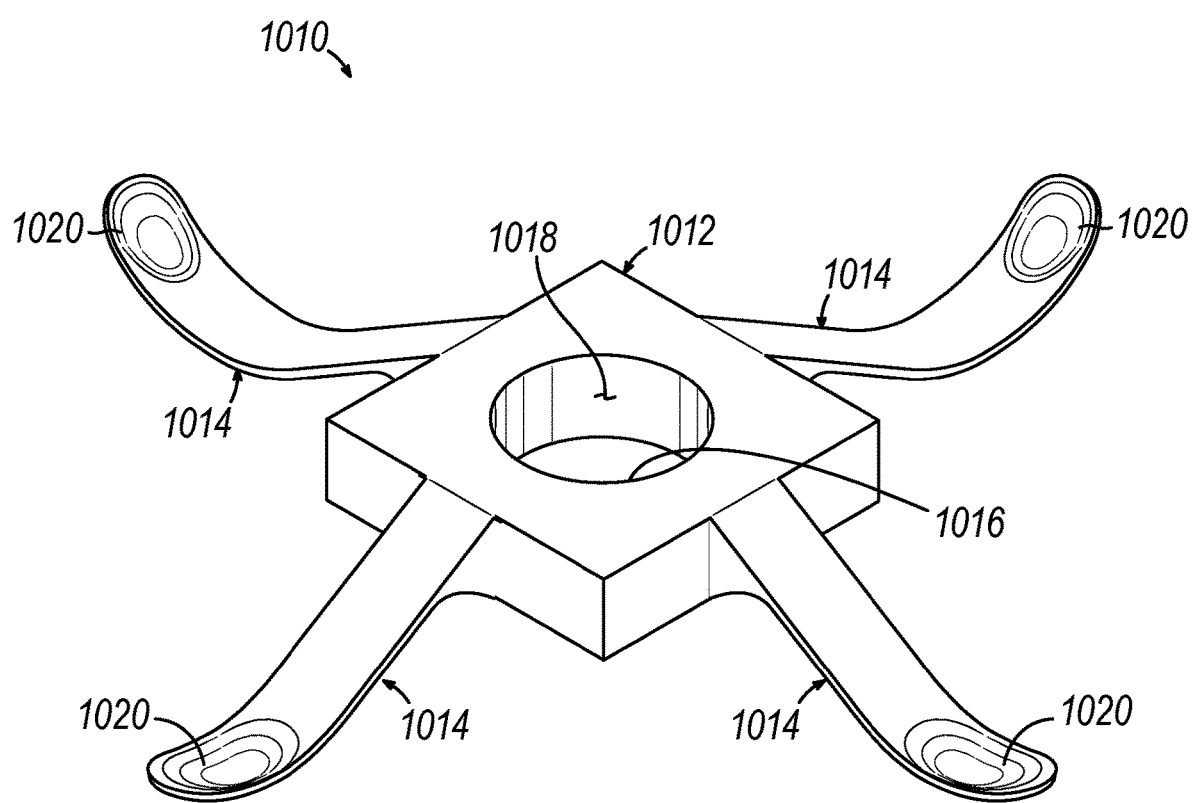
FIG. 13 depicts a perspective view of a fourth exemplary depth limiter that includes four legs.

FIG. 13 shows a perspective view of a fourth exemplary depth limiter (1010). Depth limiter (1010) includes a hub (1012) and a plurality of legs (1014). Depth limiter (1010) may be used in combination with depth limiters (210, 310, 410) described above. While hub (1012) is shown as being generally square shaped, other shapes of hub (1012) are also envisioned. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). While FIGS. 13-14B describe depth limiter (1010) with reference to cannula tube (22) of trocar (10) of FIG. 1, other cannula tubes (e.g., cannula tube (124)) may also be used. Gripping surface (1018) may be smooth or non-smooth. As shown in FIG. 13, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped portions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10). This stabilization may be achieved using mechanical spring effects of each leg (1014). Legs (1014) may have a reduced mass allowing legs (1014) to flex outwardly, causing a variable amount of spring-resistance in each direction trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (20).

Figure 14A:
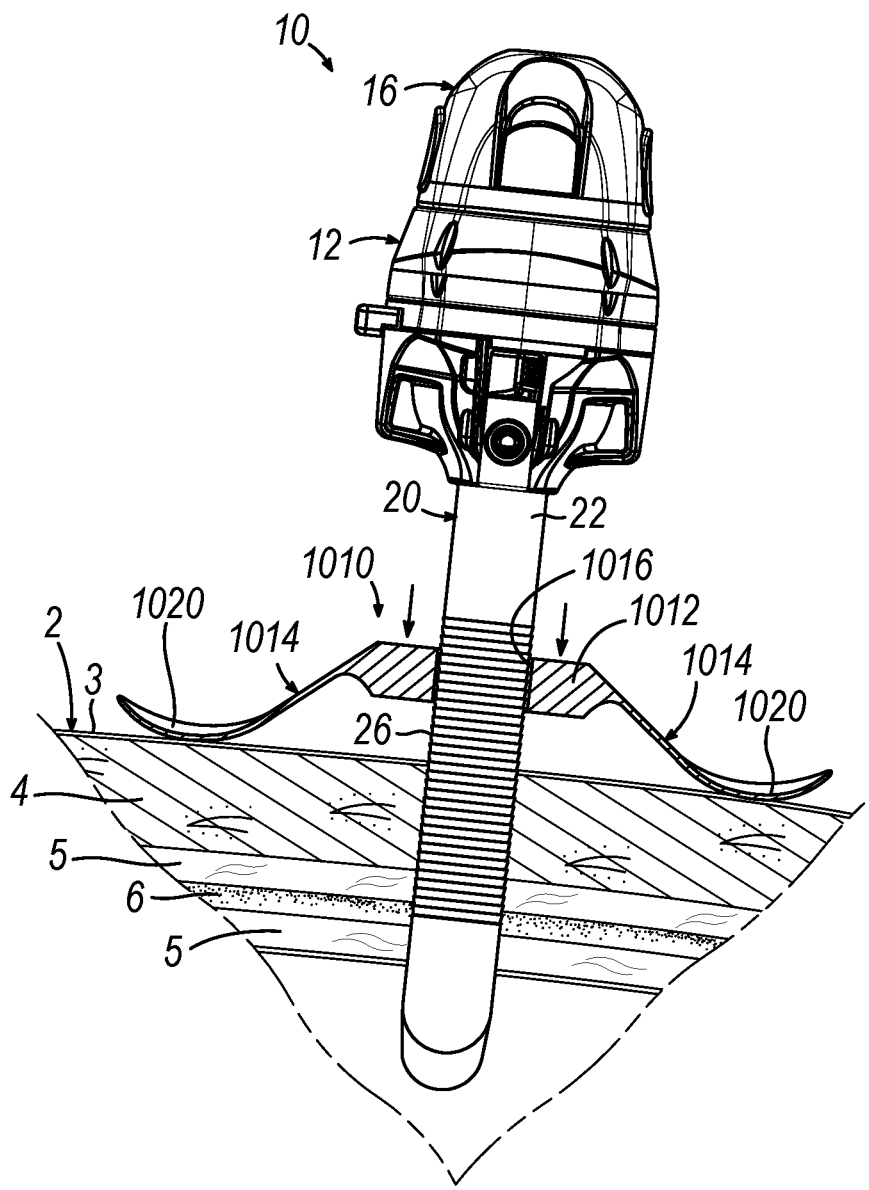
FIG. 14A depicts a partial side sectional view of the depth limiter of FIG. 13 coupled with the cannula tube of the cannula assembly of the trocar of FIG. 1, where the legs of the depth limiter are in a non-deployed configuration when the distal end of the trocar received within the abdominal cavity.
Figure 14B:
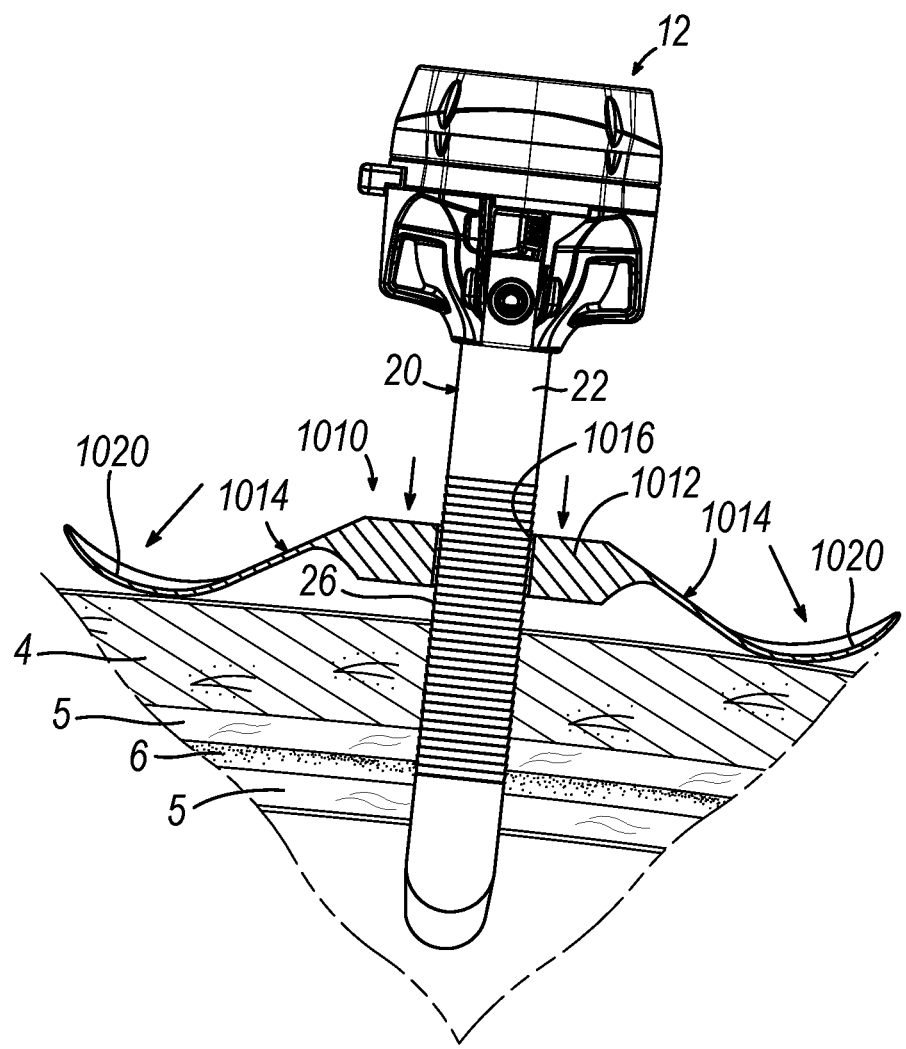
FIG. 14B depicts a partial side sectional view of the depth limiter of FIG. 13 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 14A-14B show depth limiter (1010); however, the teachings of FIGS. 14A-14B may also apply to depth limiters (1110, 1210) described in detail below. FIG. 14A shows a partial side sectional view of depth limiter (1010) of FIG. 13 coupled with cannula tube (22) of cannula assembly

(12) of trocar (10) of FIG. 1, where legs (1014) of depth limiter (1010) are in a non-deployed configuration when distal end of trocar (10) is received within abdominal cavity (1). In the non-deployed configuration (e.g., the resting configuration) of FIG. 14A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 14B shows a partial side sectional view of depth limiter (1010) of FIG. 13 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10) may achieve, and may also reduce the velocity that trocar (10) may achieve that tilt (i.e., preventing sudden accidental moves within the body). To completely undeploy depth limiter (1010) from cannula tube (22), the user may retract cannula (20) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

E. Fifth Exemplary Depth Limiter

Figure 15:
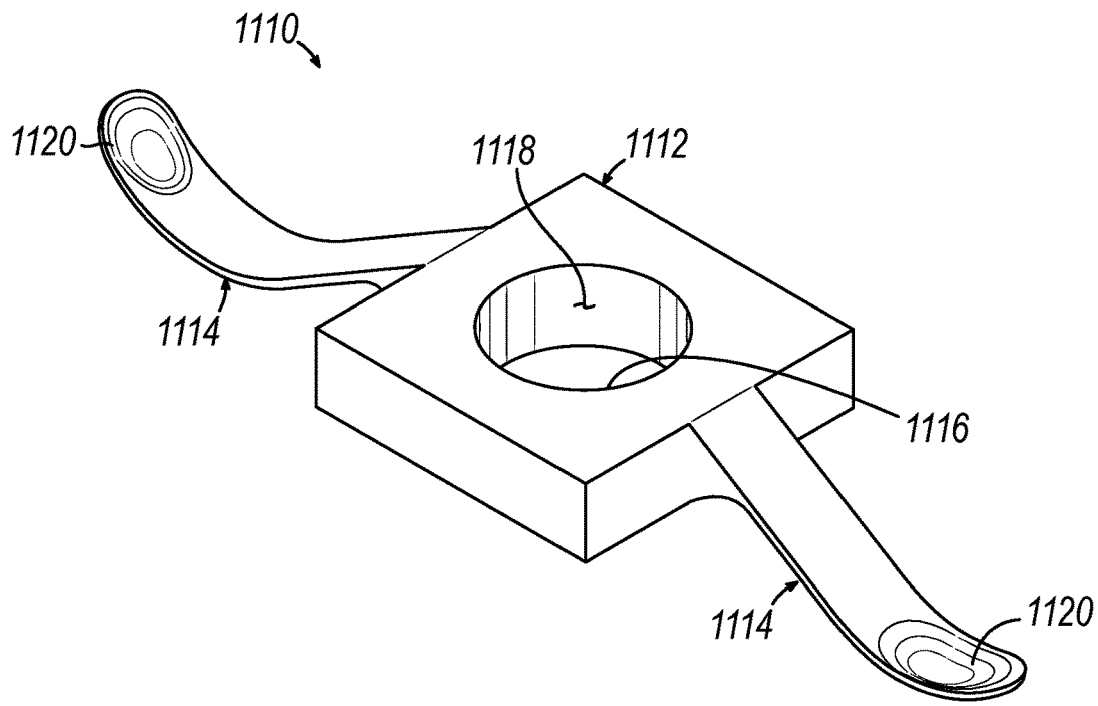
FIG. 15 depicts a perspective view of a fifth exemplary depth limiter that includes two legs.

FIG. 15 shows a fifth exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 14A-14B.

F. Sixth Exemplary Depth Limiter

Figure 16:
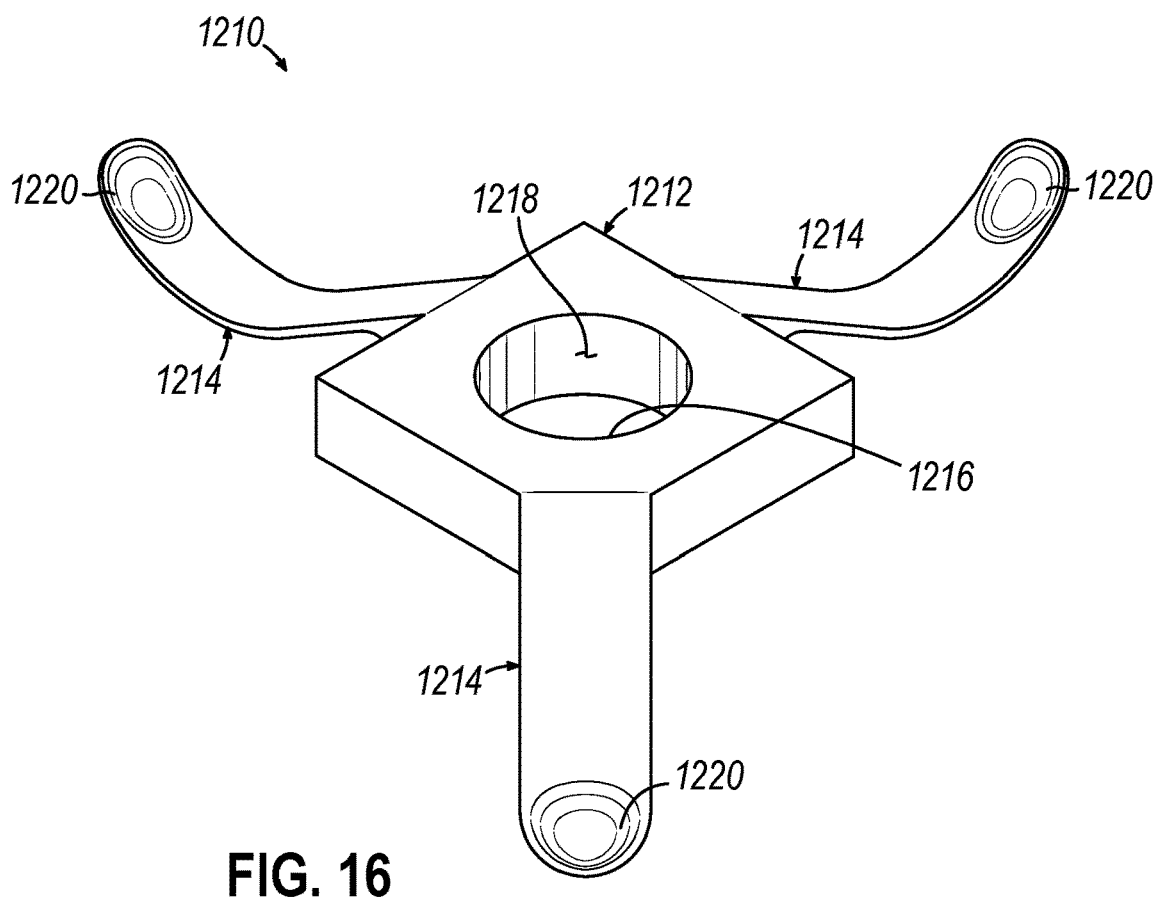
FIG. 16 depicts a perspective view of a sixth exemplary depth limiter that includes three legs.

FIG. 16 shows a sixth exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 14A-14B.

G. Seventh Exemplary Depth Limiter

FIGS. 17-19B show a seventh exemplary depth limiter (1310). Particularly, FIG. 17 shows a perspective view of depth limiter (1310). As shown, depth limiter (1310) includes a hub (1312) and a plurality of legs (1314). extending from hub (1312). Depth limiter (1310) may be used in combination with any one or more of depth limiters (210, 310, 410) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). Gripping surface (1320) may be smooth or non-smooth. As shown in FIG. 17, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1322) to distribute the downward force. As shown, legs (1314) are separated by approximately 90 degrees. Legs (1314) may be non-uniformly separated. Additionally, more or fewer legs (1314) are also envisioned (similar to those shown in FIGS. 34-35 associated with depth limiters (1110, 1210)). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120). While FIGS. 18A-19B describe depth limiter (1310) with reference to cannula tube (124) of trocar (110), cannula tube (22, 416, 616) of cannula (20, 412, 612) may also be used.

Figure 19A:
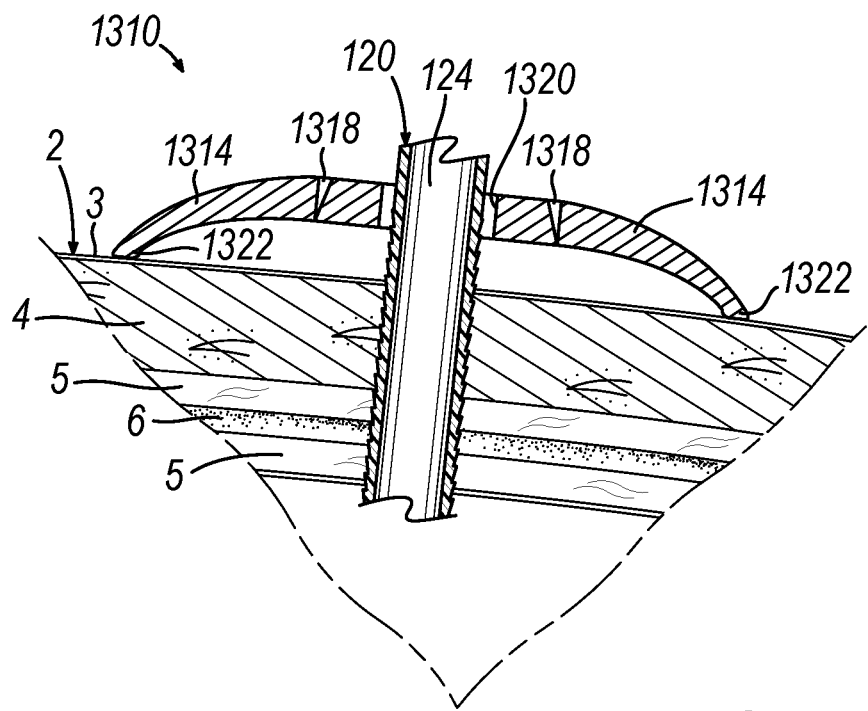
FIG. 19A depicts a partial side sectional view of the depth limiter of FIG. 17 coupled with the cannula tube of the cannula assembly of FIG. 5, where the legs of the depth limiter are in a non-deployed configuration.

FIGS. 18A and 19A show depth limiter (1310) in the movable configuration. Particularly, FIG. 18A shows a top plan view of depth limiter (1310) of FIG. 17 coupled with cannula tube (124) of cannula assembly (112) of FIG. 5, where hub (1312) of depth limiter (1310) is in a movable configuration. FIG. 19A shows a partial side sectional view of depth limiter (1310) of FIG. 17 coupled with cannula tube (124) of cannula assembly (112) of FIG. 5, where legs (1314) of depth limiter (1310) are in the movable configuration. In the movable configuration of FIGS. 37A and 38A, gripping surface (1320) forms a second effective diameter (ED2) that allows for axial movement of depth limiter (1310) relative to an outer diameter of cannula tube (124) of cannula (120). In the movable configuration, also considered the resting configuration, legs (1314) are curved downwardly. Once pushed against abdominal wall (2), legs (1314) bend flatter and provide a reaction force against abdominal wall (2) and cannula (120).

Figure 19B:
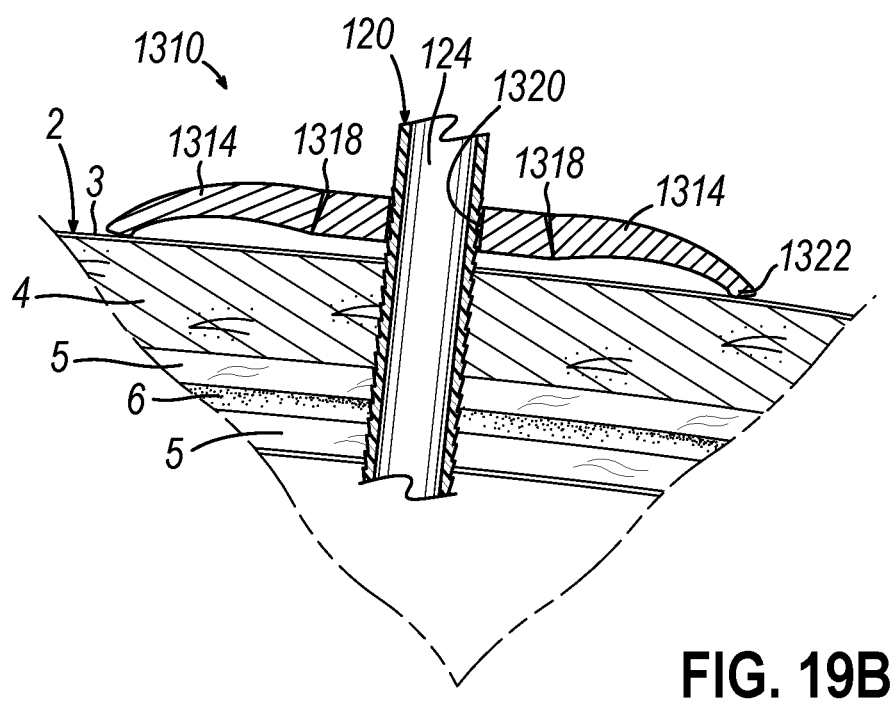
FIG. 19B depicts a partial side sectional view of the depth limiter of FIG. 17 coupled with the cannula tube of the cannula assembly of FIG. 5 following detachment and removal of the obturator, where the legs of the depth limiter are in a deployed configuration.

FIGS. 18B and 19B show depth limiter (1310) in the fixed configuration. Particularly, FIG. 18B shows a partial side sectional view of depth limiter (1310) of FIG. 17 coupled with cannula tube (124) of cannula assembly (112) of FIG. 5 following detachment and removal of obturator (116), where legs (1314) of depth limiter (1310) are in the fixed configuration. FIG. 19B shows a partial side sectional view of depth limiter (1310) of FIG. 17 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

H. Eighth Exemplary Depth Limiter

Figure 20:
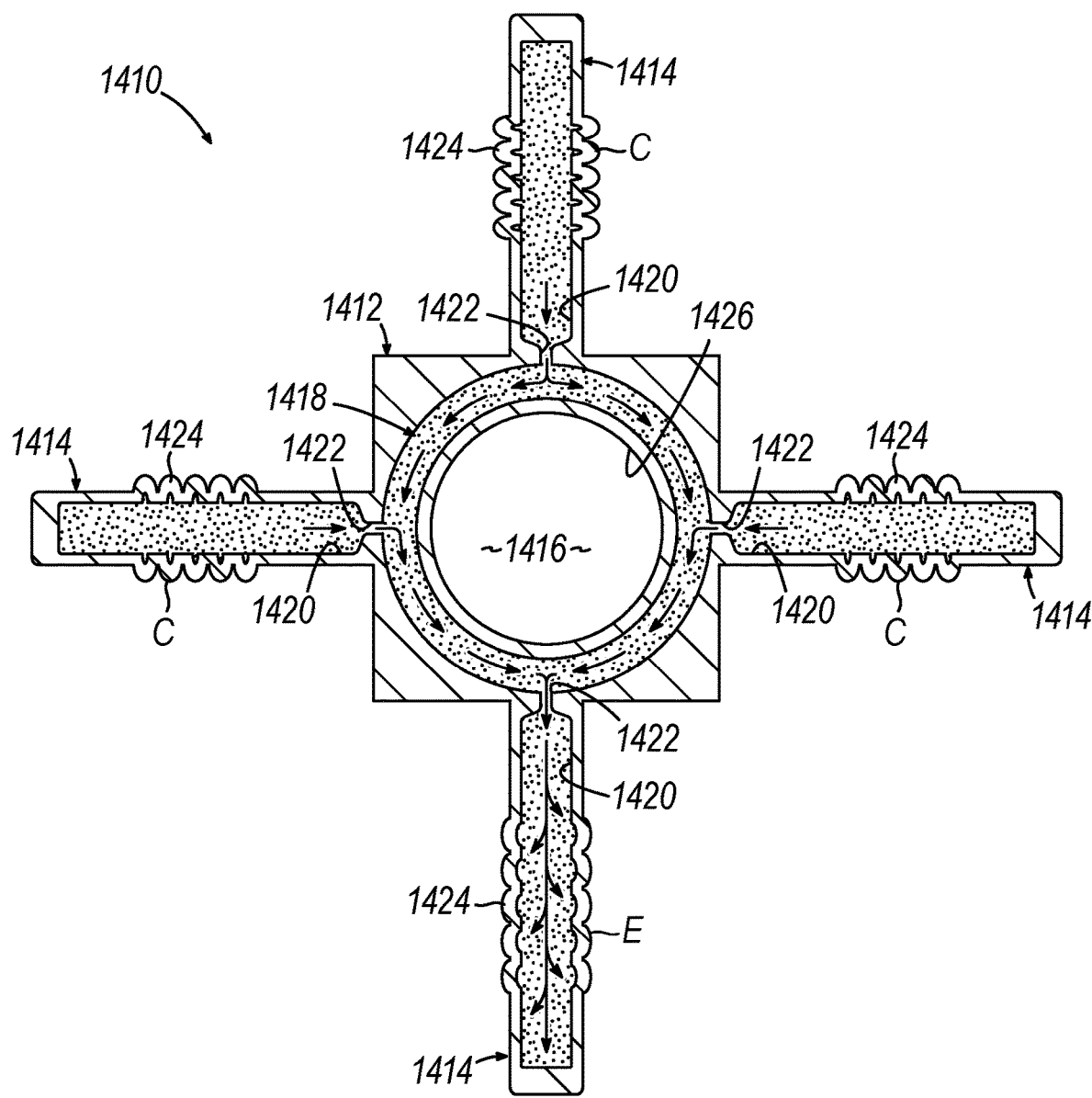
FIG. 20 depicts a top sectional view of an eighth exemplary depth limiter that includes a fluid chamber and four legs.

FIG. 20 shows a top sectional view of an eighth exemplary depth limiter (1410). Depth limiter (1410) includes a hub (1412) and a plurality of legs (1414) extending from hub (1412). Depth limiter (1410) may be used in combination with any one or more of depth limiters (210, 310, 410, 1010, 1110, 1210, 1310) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to depth limiters (1110, 1210) shown in FIGS. 15-16.

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these restricted areas (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 20, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable.

I. Exemplary Method

A method of inserting a surgical access device (e.g., trocar 10, 110) through a body wall (e.g., abdominal wall (2)) of a patient is also described. Trocar (10, 110) may include cannula (20, 120, 212, 214, 312, 314), obturator (16, 116), and one or more of depth limiters (210, 310, 410, 1010, 1110, 1210, 1310, 1410).

The method includes coupling depth limiter (210, 310, 410, 1010, 1110, 1210, 1310, 1410) with cannula tube (22, 124, 216, 218, 316, 318) of cannula (20, 120, 212, 214, 312, 314) when in the open configuration. This coupling may be obtained by the user actuating outer surfaces (228, 240, 328, 340, 428, 440) of depth limiters (210, 310, 410) which causes gripping surfaces (230, 232, 234, 242, 244, 246, 330, 332, 334, 342, 344, 346, 430, 432, 434, 442, 444, 446, 1320) to move from the fixed configuration to the open configuration. Openings (252, 254, 256, 352, 354, 356, 452, 454, 456) may be separate and discrete from one another. For example, openings (252, 352, 452) may receive cannula tubes (216, 316) having a first effective diameter (ED1), openings (254, 354, 454) may receive cannula tubes (218, 318) having a second effective diameter (ED2), and/or openings (256, 356, 456) may receive cannula tubes (22, 124) having third effective diameter (ED3). For example, first effective diameter (ED1) may be approximately 5 millimeters, where second effective diameter (ED2) may be approximately 10 millimeters, and where third effective diameter (ED3) may be approximately 12 millimeters. However, other diameters of cannula tube are also envisioned.

The method includes transitioning depth limiter (210, 310, 410, 1310) from the open configuration to a closed configuration to constrain depth limiter (210, 310, 410, 1310) axially relative to the cannula (20, 120, 212, 214, 312, 314). In the fixed configuration, gripping surfaces (230, 232, 234, 242, 244, 246, 330, 332, 334, 342, 344, 346, 430, 432, 434, 442, 444, 446, 1320) may collectively form a first effective diameter (ED1) that restricts axial movement of depth limiter (210, 310, 4101310) relative to cannula (20, 120, 212, 214, 312, 314) by directly contacting cannula (20, 120, 212, 214, 312, 314). In the open configuration, gripping surfaces (230, 232, 234, 242, 244, 246, 330, 332, 334, 342, 344, 346, 430, 432, 434, 442, 444, 446, 1320) collectively form a second effective diameter (ED2) that allows for axial movement of depth limiter (210, 310, 410, 1310) relative to cannula (20, 120, 212, 214, 312, 314).

The method may include inserting a least a portion of cannula tube (22, 124, 216, 218, 316, 318) of cannula (20, 120, 212, 214, 312, 314) into the patient. Depth limiters (210, 310, 410, 1310) may be moved along cannula (20, 120, 212, 214, 312, 314), once cannula (20, 120, 212, 214, 312, 314) is within the body by user again actuating outer surfaces (228, 240, 328, 340, 428, 440) which causes gripping surfaces (230, 232, 234, 242, 244, 246, 330, 332, 334, 342, 344, 346, 430, 432, 434, 442, 444, 446) to move from the closed configuration to the open configuration.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A depth limiter configured to couple with a first trocar cannula and a second trocar cannula, wherein the first and second trocar cannulas have different diameters, the depth limiter comprising: (a) a first body portion comprising: (i) a first gripping surface, and (ii) a second gripping surface; and (b) a second body portion, wherein the first and second body portions are pivotably coupled together and are movable between an open configuration and a closed configuration, wherein in the open configuration the first and second body portions are configured to allow for axial movement of the depth limiter relative to the first and second trocar cannulas, wherein in the closed configuration the first and second body portions are configured to restrict axial movement of the depth limiter relative to the first and second trocar cannulas, wherein the second body portion comprises: (i) a first gripping surface that together with the first gripping surface of the first body portion are configured to restrict axial movement of the depth limiter relative to the first trocar cannula in the closed configuration, and (ii) a second gripping surface that together with the second gripping surface of the first body portion are configured to restrict axial movement of the depth limiter relative to the second trocar cannula in the closed configuration.

Example 2

The depth limiter of Example 1, wherein the first gripping surfaces of the first and second body portions collectively form a first opening having a first effective diameter that are configured to selectively couple with the first trocar cannula in the closed configuration, wherein the second gripping surfaces of the first and second body portions collectively form a second opening having a second effective diameter that are configured to selectively couple with the second trocar cannula in the closed configuration, wherein the second effective diameter is greater than the first effective diameter.

Example 3

The depth limiter of Example 2, wherein the first and second openings are separate and discrete from one another.

Example 4

The depth limiter of any one or more of Examples 1 through 3, wherein the first body portion includes a third gripping surface, wherein the second body portion includes a third gripping surface that together with the third gripping surface of the first body portion collectively forms a third opening having a third effective diameter that is configured to selectively couple with a third trocar cannula, wherein the third effective diameter that is greater than either of the first and second effective diameters.

Example 5

The depth limiter of Example 4, wherein in the open configuration the depth limiter is configured to allow for axial movement of the depth limiter relative to the first, second, and third trocar cannulas, wherein in the closed configuration the depth limiter is configured to restrict axial movement of the depth limiter relative to the first, second, and third trocar cannulas.

Example 6

The depth limiter of any one or more of Examples 4 through 5, wherein the first effective diameter is approximately 5 millimeters, wherein the second effective diameter is approximately 10 millimeters, and wherein the third effective diameter is approximately 12 millimeters.

Example 7

The depth limiter of any of the preceding Examples, further comprising a living hinge disposed between the first and second body portions, wherein the first and second body portions are pivotably coupled together using the living hinge between the open and closed configurations.

Example 8

The depth limiter of Example 7, wherein the first body portion, the second body portion, and the living hinge are integrally formed together as a unitary piece.

Example 9

The depth limiter of any of the preceding Examples, further comprising a spring coupled with the first and second body portions, wherein the first and second body portions are pivotably coupled together using the spring between the open and closed configurations.

Example 10

The depth limiter of any of the preceding Examples, wherein the first gripping surface of the first body portion is spaced apart from the second gripping surface of the first body portion by a first connecting portion, wherein the first gripping surface of the second body portion is spaced apart from the second gripping surface of the second body portion by a second connecting portion.

Example 11

The depth limiter of any of the preceding Examples, wherein in the closed configuration the first gripping surface of the first body portion is spaced apart by a gap from the first gripping surface of the second body portion.

Example 12

The depth limiter of any of the preceding Examples, wherein at least one of the first or second gripping surfaces of the first and second body portions includes engagement features to lockingly engage with tissue gripping features disposed along an outer surface of the first or second trocar cannula.

Example 13

The depth limiter of Example 12, the engagement features of the first or second trocar cannula include annular ribs, wherein the tissue gripping features include parallel ridges that are configured to lockingly engage with the annular ribs of the first or second trocar cannula.

Example 14

The depth limiter of any of the preceding Examples, wherein at least one of the first or second gripping surfaces of the first and second body portions includes a smooth surface configured to frictionally engage with the first or second trocar cannula.

Example 15

The depth limiter of any of the preceding Examples, wherein the first body portion includes a first user contact portion, wherein the second body portion includes a second user contact portion, wherein the first and second body portions are configured to be actuated by a user to move the depth limiter from the closed configuration to the open configuration.

Example 16

A depth limiter configured to couple with a first trocar cannula and a second trocar cannula, wherein the first and second trocar cannulas have different diameters, the depth limiter comprising: (a) a first body portion; (b) a second body portion, wherein the first and second body portions are pivotably coupled together and are movable between an open configuration and a closed configuration, wherein in the open configuration the first and second body portions are configured to allow for axial movement of the depth limiter relative to the first or second trocar cannulas, wherein in the closed configuration the first and second body portions are configured to restrict axial movement of the depth limiter relative to the first or second trocar cannula, and (c) a plurality of openings defined the first and second body portions, wherein each opening of the plurality of openings has a different effective diameter in the closed configuration, wherein the depth limiter is configured to retain a cannula within a selected opening of the plurality of openings to restrict axial movement of the depth limiter relative to the first and second trocar cannulas in the closed configuration.

Example 17

The depth limiter of Example 16, further comprising a living hinge disposed between the first and second body portions, wherein the first and second body portions are pivotably coupled together using the living hinge between the open and closed configurations.

Example 18

The depth limiter of Example 16, wherein the first body portion, the second body portion, and the living hinge are integrally formed together as a unitary piece.

Example 19

The depth limiter of any one or more of Examples 16 through 18, further comprising a torsion spring coupled with the first and second body portions, wherein the first and second body portions are pivotably coupled together using the torsion spring between the open and closed configurations.

Example 20

A method of inserting a surgical access device through a body wall of a patient, wherein the surgical access device includes a cannula, the method comprising: (a) inserting the cannula into a first opening or a second opening of a depth limiter when the depth limiter is in an open configuration, wherein the first and second openings are separate and discrete from one another; (b) transitioning the depth limiter from the open configuration to a closed configuration to constrain the depth limiter axially relative to the cannula; and (c) inserting at least a portion of the surgical access device into the patient while using the depth limiter to prevent over insertion of surgical access device into the body wall of the patient.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, filed Mar. 26, 2021, entitled "Pinch-To-Release Cannula Depth Limiter," issued as U.S. Pat. No. 11,633,211 on Apr. 25, 2023, filed on even date herewith; U.S. patent application Ser. No. 17/213, 401, filed Mar. 26, 2021, entitled "Pinch-To-Clamp Cannula Depth Limiter," issued as U.S. Pat. No. 11,980,392 on May 14, 2024, filed on even date herewith; U.S. patent application Ser. No. 17/213,409, filed Mar. 26, 2021, entitled "Universal Size Multi-Walled Elastomer Cannula Depth Limiter," issued as U.S. Pat. No. 11,986,215 on May 21, 2024, filed on even date herewith; U.S. patent application Ser. No. 17/213,415, filed Mar. 26, 2021, entitled "Threaded Cannula Depth Limiter," issued as U.S. Pat. No. 12,213,699 on Feb. 4, 2025, filed on even date herewith; U.S. patent application Ser. No. 17/213,426, filed Mar. 26, 2021, entitled "Tilting Tang Cannula Depth Limiter," issued as U.S. Pat. No. 11,712,267 on Aug. 1, 2023, filed on even date herewith; U.S. patent application Ser. No. 17/213,431, filed Mar. 26, 2021, entitled "Two Piece Separable Obturator," issued as U.S. Pat. No. 11,980,393 on May 14, 2024, filed on even date herewith; U.S. patent application Ser. No. 17/213,434, filed Mar. 26, 2021, entitled "Latchless Obturator with Interference Fit Feature," issued as U.S. Pat. No. 11,974,773 on May 7, 2024, filed on even date herewith; U.S. patent application Ser. No. 17/213,437, filed Mar. 26, 2021, entitled "Balancing Feature for Reusable Trocar," issued as U.S. Pat. No. 11,559,329 on Jan. 24, 2023, filed on even date herewith; U.S. patent application Ser. No. 17/213,508, filed Mar. 26, 2021, entitled "Airflow Channels and Patterns in Lumen for Cannula," issued as U.S. Pat. No. 12,035,841 on Jul. 16, 2024, filed on even date herewith; and/or U.S. patent application Ser. No. 17/213,518, filed Mar. 26, 2021, entitled "Stabilizer for Surgical Shafts or Cannulas," issued as U.S. Pat. No. 12,042,342 on Jul. 23, 2024, filed on even date herewith. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A depth limiter configured to couple with a first trocar cannula and a second trocar cannula, wherein the first and second trocar cannulas have different diameters, the depth limiter comprising:
   (a) a first body portion comprising:
      (i) a first gripping surface, and
      (ii) a second gripping surface; and
   (b) a second body portion, wherein the first and second body portions are pivotably coupled together by a living hinge and are movable between an open configuration and a closed configuration, wherein in the open configuration the first and second body portions are configured to allow for axial movement of the depth limiter relative to the first and second trocar cannulas, wherein in the closed configuration the first and second body portions are configured to restrict axial movement of the depth limiter relative to the first and second trocar cannulas, wherein the second body portion comprises:
- (i) a first gripping surface that together with the first gripping surface of the first body portion collectively form a first opening having a first effective diameter that is sized to receive and configured to restrict axial movement of the depth limiter relative to the first trocar cannula in the closed configuration, and
- (ii) a second gripping surface that together with the second gripping surface of the first body portion collectively form a second opening having a second effective diameter that is sized to receive and configured to restrict axial movement of the depth limiter relative to the second trocar cannula in the closed configuration, wherein the second effective diameter is greater than the first effective diameter, wherein the second opening opens up to an exterior of the depth limiter disposed opposite the living hinge to expose an outer surface of the second trocar cannula in the open and closed configurations, wherein the living hinge defines a free terminal end of the depth limiter and is configured to bias the first and second body portions toward the closed configuration, wherein the living hinge comprises a notch in an exterior surface of the depth limiter.

2. The depth limiter of claim 1, wherein the first and second openings are separate and discrete from one another.

3. The depth limiter of claim 1, wherein the first body portion includes a third gripping surface, wherein the second body portion includes a third gripping surface that together with the third gripping surface of the first body portion collectively forms a third opening having a third effective diameter that is configured to selectively couple with a third trocar cannula, wherein the third effective diameter is smaller than either of the first and second effective diameters.

4. The depth limiter of claim 3, wherein in the open configuration the depth limiter is configured to allow for axial movement of the depth limiter relative to the first, second, and third trocar cannulas, wherein in the closed configuration the depth limiter is configured to restrict axial movement of the depth limiter relative to the first, second, and third trocar cannulas.

5. The depth limiter of claim 3, wherein the first effective diameter is approximately 10 millimeters, wherein the second effective diameter is approximately 12 millimeters, and wherein the third effective diameter is approximately 5 millimeters.

6. The depth limiter of claim 1, wherein the first body portion, the second body portion, and the living hinge are integrally formed together as a unitary piece.

7. The depth limiter of claim 1, wherein the first gripping surface of the first body portion is spaced apart from the second gripping surface of the first body portion by a first connecting portion, wherein the first gripping surface of the second body portion is spaced apart from the second gripping surface of the second body portion by a second connecting portion.

8. The depth limiter of claim 1, wherein in the closed configuration the first gripping surface of the first body portion is spaced apart by a gap from the first gripping surface of the second body portion.

9. The depth limiter of claim 1, wherein at least one of the first or second gripping surfaces of the first and second body portions includes engagement features configured to lockingly engage with tissue gripping features disposed along an outer surface of the first or second trocar cannula.

10. The depth limiter of claim 9, wherein the tissue gripping features of the first or second trocar cannula include annular ribs, wherein the engagement features include parallel ridges that are configured to lockingly engage with the annular ribs of the first or second trocar cannula.

11. The depth limiter of claim 1, wherein the first body portion includes a first user contact portion, wherein the second body portion includes a second user contact portion, wherein the first and second body portions are configured to be actuated by a user at the first and second user contact portions to move the depth limiter from the closed configuration to the open configuration.

12. A surgical assembly, comprising
- (a) a trocar having a trocar cannula; and
- (b) a depth limiter configured to couple with the trocar cannula, the depth limiter comprising:
  - (i) a first body portion that includes first and second gripping surfaces,
  - (ii) a second body portion that includes first and second gripping surfaces, wherein the first and second body portions are pivotably coupled together by a living hinge and are movable between an open configuration and a closed configuration, wherein in the open configuration the first and second body portions are configured to allow for axial movement of the depth limiter relative to the trocar cannula, wherein in the closed configuration the first and second body portions are configured to restrict axial movement of the depth limiter relative to the trocar cannula, and
  - (iii) a plurality of openings defined by and between the first and second body portions, wherein the plurality of openings includes first and second openings, wherein the depth limiter is configured to retain the trocar cannula within one of the first or second openings to restrict axial movement of the depth limiter relative to the trocar cannula in the closed configuration, wherein the second opening opens up to an exterior of the depth limiter disposed opposite the living hinge to expose an outer surface of the trocar cannula in the open and closed configurations, wherein the living hinge defines a free terminal end of the depth limiter and is configured to bias the first and second body portions toward the closed configuration, wherein the living hinge comprises a notch in an exterior surface of the depth limiter.

13. The depth limiter of claim 1, wherein the second gripping surfaces of the first and second body portions are disposed further from the living hinge than the first gripping surfaces of the first and second body portions.

14. The depth limiter of claim 12, wherein the second gripping surfaces of the first and second body portions are disposed further from the living hinge than the first gripping surfaces of the first and second body portions.

15. The depth limiter of claim 12, wherein the first opening is collectively formed by the first gripping surfaces of the first and second body portions to define a first area in the closed configuration, wherein the second opening is collectively formed by the second gripping surfaces of the first and second body portions to define a second area in the closed configuration that is greater than the first area in the closed configuration.

16. A surgical assembly, comprising:
- (a) a first trocar having a first trocar cannula with a first maximum diameter;

(b) a second trocar having a second trocar cannula with a second maximum diameter; and (c) a depth limiter configured to independently couple with each of the first trocar cannula and the second trocar cannula, the depth limiter comprising:

(i) a first body portion comprising:

(A) a first gripping surface, and (B) a second gripping surface; and (ii) a second body portion, wherein the first and second body portions are pivotably coupled together by a living hinge and are movable between an open configuration and a closed configuration, wherein in the open configuration the first and second body portions are configured to allow for axial movement of the depth limiter relative to the first and second trocar cannulas, wherein in the closed configuration the first and second body portions are configured to restrict axial movement of the depth limiter relative to the first and second trocar cannulas, wherein the second body portion comprises:

(A) a first gripping surface that together with the first gripping surface of the first body portion collectively form a first opening having a first effective diameter that is sized to receive and configured to restrict axial movement of the depth limiter relative to the first trocar cannula in the closed configuration, and (B) a second gripping surface that together with the second gripping surface of the first body portion collectively form a second opening having a second effective diameter that is sized to receive and configured to restrict axial movement of the depth limiter relative to the second trocar cannula in the closed configuration, wherein the second effective diameter is greater than the first effective diameter, wherein an open space between the first and second openings in each of the open and closed configurations increases in size in a direction away from the living hinge, wherein the second gripping surfaces of the first and second body portions at least partially open up to an exterior of the depth limiter to expose an outer surface of the second trocar cannula in the open and closed configurations, wherein the living hinge defines a free terminal end of the depth limiter and is configured to bias the first and second body portions toward the closed configuration, wherein the living hinge comprises a notch in an exterior surface of the depth limiter.

17. The depth limiter of claim 16, wherein the second gripping surfaces of the first and second body portions are disposed further from the living hinge than the first gripping surfaces of the first and second body portions.

* * * * *